US007482301B2

(12) United States Patent
Boussie et al.

(10) Patent No.: US 7,482,301 B2
(45) Date of Patent: Jan. 27, 2009

(54) TITANIUM SUBSTITUTED PYRIDYL AMINE COMPLEXES, CATALYSTS AND PROCESSES FOR POLYMERIZING ETHYLENE AND STYRENE

(75) Inventors: Thomas R. Boussie, Menlo Park, CA (US); Gary M. Diamond, San Jose, CA (US); Christopher Goh, North Adams, MA (US); Anne M. LaPointe, Sunnyvale, CA (US); Margarete K. Leclerc, Santa Clara, CA (US); Cheryl Lund, Milpitas, CA (US)

(73) Assignee: Symyx Technologies, Inc.

( * ) Notice: Subject to any disclaimer, the term of this patent is extended or adjusted under 35 U.S.C. 154(b) by 216 days.

(21) Appl. No.: 11/642,290

(22) Filed: Dec. 19, 2006

(65) Prior Publication Data

US 2007/0100145 A1 May 3, 2007

Related U.S. Application Data

(62) Division of application No. 11/081,355, filed on Mar. 16, 2005, now Pat. No. 7,157,400, which is a division of application No. 10/287,129, filed on Nov. 4, 2002, now Pat. No. 7,122,689.

(60) Provisional application No. 60/332,880, filed on Nov. 6, 2001.

(51) Int. Cl.
*B01J 31/02* (2006.01)
*B01J 31/18* (2006.01)
*C08F 4/64* (2006.01)

(52) U.S. Cl. .................. 502/167; 502/103; 502/152; 502/155

(58) Field of Classification Search .................. 502/103, 502/152, 155, 167
See application file for complete search history.

(56) References Cited

U.S. PATENT DOCUMENTS

| | | | |
|---|---|---|---|
| 5,064,802 A | 11/1991 | Stevens et al. |
| 5,153,157 A | 10/1992 | Hlatky et al. |
| 5,453,410 A | 9/1995 | Kolthammer et al. |
| 5,599,761 A | 2/1997 | Turner |
| 5,616,664 A | 4/1997 | Timmers et al. |
| 5,631,391 A | 5/1997 | Canich |
| 5,637,660 A | 6/1997 | Nagy et al. |
| 5,985,356 A | 11/1999 | Schultz et al. |
| 6,030,917 A | 2/2000 | Weinberg et al. |
| 6,103,657 A | 8/2000 | Murray |
| 6,489,168 B1 | 12/2002 | Wang et al. |
| 6,548,026 B1 | 4/2003 | Dales et al. |
| 6,706,829 B2 | 3/2004 | Boussie et al. |
| 6,713,577 B2 | 3/2004 | Boussie et al. |
| 6,727,361 B2 | 4/2004 | LaPointe et al. |
| 6,750,345 B2 | 6/2004 | Boussie et al. |
| 6,828,397 B2 | 12/2004 | Boussie et al. |
| 7,157,400 B2 | 1/2007 | Boussie et al. |
| 2002/0142912 A1 | 10/2002 | Boussie et al. |
| 2004/0122247 A1 | 6/2004 | Boussie et al. |
| 2004/0209765 A1 | 10/2004 | Boussie et al. |

FOREIGN PATENT DOCUMENTS

| | | |
|---|---|---|
| EP | 0 277 004 | 8/1988 |
| EP | 1 364 974 | 11/2003 |
| JP | 2001-48909 | 2/2001 |
| JP | 2001-48910 | 2/2001 |
| WO | WO 98/03521 | 1/1998 |
| WO | WO 99/06413 | 2/1999 |
| WO | WO 99/42467 | 8/1999 |
| WO | WO 02/38628 | 5/2002 |
| WO | WO 02/46249 | 6/2002 |

OTHER PUBLICATIONS

Bercaw et al., A New Class of Zirconocene Catalysts For The Syndiospecific Polymerization Of Prolyene And Its Modification For Varying Polypropylene From Isotactic To Syndiotactic, J. Am. Chem. Soc., 1996, 118, pp. 11988-11989.

Bercaw et al., "Mechanisms of Sterocontrol For Doubly Silylene-Bridged . . . " J. Am. Chem. Soc., 1999, 121, pp. 564-573.

Brintzinger et al., "Stereospecific Olefin Polymerization With Chiral Metallocene Catalysts," Angew. Chem. Int. Ed. Engl., 1995, 34, pp. 1143-1170.

Coates et al., "Development of a Diversity-Based Approach For The Discovery of Steroselective Polymerization Catalysts," Angew. Chem. Int. Ed. Engl., 2000, 39, pp. 3626-3629.

Gibson et al., The Search For New Generation Olefin Polymerization Catalysts: Life Beyond Metallocenes, Angew. Chem. Int. Ed. Engl., 1999, 38, pp. 428-447.

Jordan, "Chemistry of Cationic Dicyclopentadienyl Group 4 Metal-Alkyl Complexes," Adv. Organometallic Chem., 1991, 32, pp. 325-387.

LaPointe, "New Family of Weakly Coordinating Anions," J. Am. Chem. Soc., 2000, 122, pp. 9560-9561.

(Continued)

*Primary Examiner*—Caixia Lu
(74) *Attorney, Agent, or Firm*—Armstrong Teasdale LLP

(57) ABSTRACT

New compositions, titanium-ligand complexes and arrays with pyridyl-amine ligands are disclosed that catalyze the polymerization of monomers into polymers. These catalysts with titanium metal centers have high performance characteristics, including high styrene incorporation into ethylene/styrene copolymers.

7 Claims, No Drawings

OTHER PUBLICATIONS

Piers et al., "New Bifunctional Perfluoroaryl Boranes: Synthesis And Reactivity of the Ortho-Phenylene-Bridged Diboranes . . . " J. Am. Chem. Soc., 1999, 121, pp. 3244-3245.

Schrock et al., "Synthesis of Titanium, Zirconium, and Hafnium Complexes That Contain Diamido Donor Ligands of the Type . . . " Adv. Organomteallic Chem., 1999, 18, pp. 3649-3670.

Kang et al., The Synthesis and Polymerization Behavior of Bimetallic Pyridine Diamide Complexes Containing Transition Metal (Ti, Zr), J. of Poly. Sci., 1999, 37, pp. 3756-3762.

Guerin et al., "Conformationally Rigid Diamide Complexes: Synthesis and Structure of Titanium(IV) Alkyl Derivatives," Organometallics, 1996, 15, pp. 5085-5089.

Guerin et al., "Synthesis, Structure, and Reactivity of Titanacyclopentadiene Complexes Bearing Ancillary Pyridine Diamide Ligands," Organometallics, 1997, 16, pp. 1491-1496.

TITANIUM SUBSTITUTED PYRIDYL AMINE COMPLEXES, CATALYSTS AND PROCESSES FOR POLYMERIZING ETHYLENE AND STYRENE

RELATED APPLICATIONS

This application is a divisional application of U.S. Ser. No. 11/081,355 filed Mar. 16, 2005, now issued as U.S. Pat. No. 7,157,400, which is a divisional application of U.S. Ser. No. 10/287,129 filed Nov. 4, 2002, now U.S. Pat. No. 7,122,689 which claims the benefit of U.S. Ser. No. 60/332,880 filed Nov. 6, 2001 and now expired, both of which are incorporated herein by reference.

FIELD OF THE INVENTION

The present invention relates to titanium complexes, compositions and/or catalysts that provide enhanced olefin polymerization performance for the copolymerization of ethylene and styrene, leading to polymers having novel, improved or desired properties.

BACKGROUND OF THE INVENTION

Ancillary (or spectator) ligand-metal coordination complexes (e.g. organometallic complexes) and compositions are useful as catalysts, additives, stoichiometric reagents, monomers, solid state precursors, therapeutic reagents and drugs. Ancillary ligand-metal coordination complexes of this type can be prepared by combining an ancillary ligand with a suitable metal compound or metal precursor in a suitable solvent at a suitable temperature. The ancillary ligand contains functional groups that bind to the metal center(s), remain associated with the metal center(s), and therefore provide an opportunity to modify the steric, electronic and chemical properties of the active metal center(s) of the complex.

Certain known ancillary ligand-metal complexes and compositions are catalysts for reactions such as oxidation, reduction, hydrogenation, hydrosilylation, hydrocyanation, hydroformylation, polymerization, carbonylation, isomerization, metathesis, carbon-hydrogen activation, carbon-halogen activation, cross-coupling, Friedel-Crafts acylation and alkylation, hydration, dimerization, trimerization, oligomerization, Diels-Alder reactions and other transformations.

One example of the use of these types of ancillary ligand-metal complexes and compositions is in the field of polymerization catalysis. In connection with single site catalysis, the ancillary ligand typically offers opportunities to modify the electronic and/or steric environment surrounding an active metal center. This allows the ancillary ligand to assist in the creation of possibly different polymers. Group 4 metallocene based single site catalysts are generally known for polymerization reactions. See, generally, "Chemistry of Cationic Dicyclopentadienyl Group 4 Metal-Alkyl Complexes", Jordan, *Adv. Organometallic Chem.*, 1991, Vol. 32, pp. 325-153 and "Stereospecific Olefin Polymerization with Chiral Metallocene Catalysts", Brintzinger, et al., *Angew. Chem. Int. Ed. Engl.*, 1995, Vol. 34, pp. 1143-1170, and the references therein, all of which is incorporated herein by reference.

However, those of skill in the art of single site catalysis appreciate that there may be substantial differences in performance between different metal centers. For example, U.S. Pat. No. 5,064,802 discloses a broad category of mono-cyclopentadienyl ligand catalysts with a broad disclosure f useful metals, and U.S. Pat. No. 5,631,391 more specifically discloses that titanium metal centers offer performance advantages with respect to the same or similar ligands. Additionally, Coates, et al., *Angew. Chem. Int. Ed.*, 2000, vol. 39, pp. 3626-3629 describes the unpredictable nature of olefin polymerization catalyst structure-activity relationships. Moreover, given the extensive research activities with respect to cyclopentadienyl ligand catalysts, there is continued interested in the next generation of non-cyclopentadienyl ligands for olefin polymerization catalysts providing attractive alternatives. See, e.g., "The Search for New-Generation Olefm Polymerization Catalysts: Life beyond Metallocenes", Gibson, et al., *Angew. Chem. Int. Ed.*, 1999, vol. 38, pp. 428-447; *Organometallics* 1999, 18, pp. 3649-3670. Indeed, many such systems have been discovered, see, e.g., U.S. Pat. No. 5,637,660.

Previously disclosed applications for pyridyl amine ligand-based catalysts have focused on zirconium complexes of substituted pyridyl amine ligands for olefin polymerization in general. See, e.g., U.S. Pat. No. 6,103,657. It has now surprisingly been found that titanium metal based substituted pyridyl amine catalysts with particular substituents have enhanced performance for the copolymerization of ethylene and styrene.

SUMMARY OF THE INVENTION

This invention discloses surprising enhanced catalytic performances for olefin polymerization when certain combinations of ligands and titanium metal precursors are employed. Specifically, this invention discloses both the preferred use of a titanium metal center and certain pyridyl-amine ligands. Such combinations lead to new ligand-metal complexes, catalyst compositions and processes for the polymerization of olefins, diolefuis, or other polymerizable monomers. In particular, copolymers of ethylene and styrene may be prepared with relatively high incorporation of the styrene into the polymer backbone, and high weight-average molecular weight (Mw). Thus, polymers having novel, improved or desired properties may be prepared using the catalysts and processes of this invention.

The invention disclosed herein additionally includes catalysts comprising ancillary ligand-titanium complexes, and optionally activators, that catalyze polymerization and copolymerization reactions, particularly with monomers that are olefms, diolefins or other unsaturated compounds. Titanium complexes, compositions or compounds using the disclosed ligands are within the scope of this invention. The titanium-ligand complexes maybe in a neutral or charged state. The ligand to titanium ratio may also vary, the exact ratio being dependent on the nature of the ligand and metal-ligand complex. The titanium-ligand complex or complexes may take different forms, for example, they may be monomeric, dimeric or higher orders thereof. In another aspect of the invention, a polymerization process is disclosed for monomers.

The polymerization process involves subjecting one or more monomers to the catalyst compositions or complexes of this invention under polymerization conditions. The polymerization process can be continuous, batch or semi-batch and can be homogeneous, supported homogeneous or heterogeneous. Another aspect of this invention relates to arrays of ligands, titanium precursors and/or titanium-ligand complexes. These arrays are useful for the high speed or combinatorial materials science discovery or optimization of the catalyst compositions or complexes disclosed herein.

Further aspects of this invention will be evident to those of skill in the art upon review of this specification.

Thus, it is a feature of this invention to use titanium-ligand complexes as polymerization catalysts with enhanced performance.

It is a further object of this invention to polymerize olefins and unsaturated monomers with titanium-ligand complexes.

It is still a further object of this invention to polymerize olefins and unsaturated monomers with the titanium-ligand complexes that additionally comprise an activator or combination of activators.

DETAILED DESCRIPTION OF THE INVENTION

The inventions disclosed herein include titanium metal complexes and compositions, which are useful as catalysts for polymerization reactions.

As used herein, the phrase "characterized by the formula" is not intended to be limiting and is used in the same way that "comprising" is commonly used. The term "independently selected" is used herein to indicate that the R groups, e.g., $R^1$, $R^2$, $R^3$, $R^4$, and $R^5$ can be identical or different (e.g. $R^1$, $R^2$, $R^3$, $R^4$, and $R^5$ may all be substituted alkyls or $R^1$ and $R^2$ may be a substituted alkyl and $R^3$ may be an aryl, etc.). Use of the singular includes use of the plural and vice versa (e.g., a hexane solvent, includes hexanes). A named R group will generally have the structure that is recognized in the art as corresponding to R groups having that name. The terms "compound" and "complex" are generally used interchangeably in this specification, but those of skill in the art may recognize certain compounds as complexes and vice versa. For the purposes of illustration, representative certain groups are defined herein. These definitions are intended to supplement and illustrate, not preclude, the definitions known to those of skill in the art.

The terms "halo", "halide" or "halogen" all refer to F, Cl, Br or I.

"Hydrocarbyl" refers to univalent hydrocarbyl radicals containing 1 to about 30 carbon atoms, preferably 1 to about 24 carbon atoms, most preferably 1 to about 12 carbon atoms, including branched or unbranched, saturated or unsaturated species, such as alkyl groups, alkenyl groups, aryl groups, and the like. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom.

The term "alkyl" is used herein to refer to a branched or unbranched, saturated or unsaturated acyclic hydrocarbon radical. Suitable alkyl radicals include, for example, methyl, ethyl, n-propyl, i-propyl, 2-propenyl (or allyl), vinyl, n-butyl, t-butyl, i-butyl (or 2-methylpropyl), etc. In particular embodiments, alkyls have between 1 and 200 carbon atoms, between 1 and 50 carbon atoms or between 1 and 20 carbon atoms.

"Substituted alkyl" refers to an alkyl as just described in which one or more hydrogen atom bound to any carbon of the alkyl is replaced by another group such as a halogen, aryl, substituted aryl, cycloalkyl, substituted cycloalkyl, heterocycloalkyl, substituted heterocycloalkyl, halogen, alkylhalos (e.g., $CF_3$), hydroxy, amino, phosphido, alkoxy, amino, thio, nitro, and combinations thereof. Suitable substituted alkyls include, for example, benzyl, trifluoromethyl and the like.

The term "heteroalkyl" refers to an alkyl as described above in which one or more hydrogen atoms to any carbon of the alkyl is replaced by a heteroatom selected from the group consisting of N, O, P, B, S, Si, Sb, Al, Sn, As, Se and Ge. This same list of heteroatoms is useful throughout this specification. The bond between the carbon atom and the heteroatom may be saturated or unsaturated. Thus, an alkyl substituted with a heterocycloalkyl, substituted heterocycloalkyl, heteroaryl, substituted heteroaryl, alkoxy, aryloxy, boryl, phosphino, amino, silyl, thio, or seleno is within the scope of the term heteroalkyl. Suitable heteroalkyls include cyano, benzoyl, 2-pyridyl, 2-furyl and the like.

The term "cycloalkyl" is used herein to refer to a saturated or unsaturated cyclic non-aromatic hydrocarbon radical having a single ring or multiple condensed rings. Suitable cycloalkyl radicals include, for example, cyclopentyl, cyclohexyl, cyclooctenyl, bicyclooctyl, etc. In particular embodiments, cycloalkyls have between 3 and 200 carbon atoms, between 3 and 50 carbon atoms or between 3 and 20 carbon atoms.

"Substituted cycloalkyl" refers to cycloalkyl as just described including in which one or more hydrogen atom to any carbon of the cycloalkyl is replaced by another group such as a halogen, alkyl, substituted alkyl, aryl, substituted aryl, cycloalkyl, substituted cycloalkyl, heterocycloalkyl, substituted heterocycloalkyl, heteroaryl, substituted heteroaryl, alkoxy, aryloxy, boryl, phosphino, amino, silyl, thio, seleno and combinations thereof. Suitable substituted cycloalkyl radicals include, for example, 4-dimethylaminocyclohexyl, 4,5-dibromocyclohept 4-enyl, and the like.

The term "heterocycloalkyl" is used herein to refer to a cycloalkyl radical as described, but in which one or more or all carbon atoms of the saturated or unsaturated cyclic radical are replaced by a heteroatom such as nitrogen, phosphorous, oxygen, sulfur, silicon, germanium, selenium, or boron. Suitable heterocycloalkyls include, for example, piperazinyl, morpholinyl, tetrahydropyranyl, tetrahydrofuranyl, piperidinyl, pyrrolidinyl, oxazolinyl and the like.

"Substituted heterocycloalkyl" refers to heterocycloalkyl as just described including in which one or more hydrogen atom to any atom of the heterocycloalkyl is replaced by another group such as a halogen, alkyl, substituted alkyl, aryl, substituted aryl, heteroaryl, substituted heteroaryl, alkoxy, aryloxy, boryl, phosphino, amino, silyl, thio, seleno and combinations thereof. Suitable substituted heterocycloalkyl radicals include, for example, N-methylpiperazinyl, 3-dimethylaminomorpholinyl and the like.

The term "aryl" is used herein to refer to an aromatic substituent which may be a single aromatic ring or multiple aromatic rings which are fused together, linked covalently, or linked to a common group such as a methylene or ethylene moiety. The aromatic ring(s) may include phenyl, naphthyl, anthracenyl, and biphenyl, among others. In particular embodiments, aryls have between 1 and 200 carbon atoms, between 1 and 50 carbon atoms or between 1 and 20 carbon atoms.

"Substituted aryl" refers to aryl as just described in which one or more hydrogen atom bound to any carbon is replaced by one or more functional groups such as alkyl, substituted alkyl, cycloalkyl, substituted cycloalkyl, heterocycloalkyl, substituted heterocycloalkyl, halogen, alkylhalos (e.g., $CF_3$), hydroxy, amino, phosphido, alkoxy, amino, thio, nitro, and both saturated and unsaturated cyclic hydrocarbons which are fused to the aromatic ring(s), linked covalently or linked to a common group such as a methylene or ethylene moiety. The common linking group may also be a carbonyl as in benzophenone or oxygen as in diphenylether or nitrogen in diphenylamine.

The term "heteroaryl" as used herein refers to aromatic rings in which one or more carbon atoms of the aromatic ring(s) are replaced by a heteroatom(s) such as nitrogen, oxygen, boron, selenium, phosphorus, silicon or sulfur. Heteroaryl refers to structures that may be a single aromatic ring, multiple aromatic ring(s), or one or more aromatic rings coupled to one or more non-aromatic ring(s). In structures having multiple rings, the rings can be fused together, linked covalently, or linked to a common group such as a methylene or ethylene moiety. The common linking group may also be a carbonyl as in phenyl pyridyl ketone. As used herein, rings such as thiophene, pyridine, isoxazole, pyrazole, pyrrole, furan, etc. or benzo-fused analogues of these rings are defined by the term "heteroaryl."

"Substituted heteroaryl" refers to heteroaryl as just described including in which one or more hydrogen atoms bound to any atom of the heteroaryl moiety is replaced by another group such as a halogen, alkyl, substituted alkyl, aryl, substituted aryl, heteroaryl, substituted heteroaryl, alkoxy, aryloxy, boryl, phosphino, amino, silyl, thio, seleno and combinations thereof. Suitable substituted heteroaryl radicals include, for example, 4-N,N-dimethylaminopyridine.

The term "alkoxy" is used herein to refer to the —OZ$^1$ radical, where Z$^1$ is selected from the group consisting of alkyl, substituted alkyl, cycloalkyl, substituted cycloalkyl, heterocylcoalkyl, substituted heterocycloalkyl, silyl groups and combinations thereof as described herein. Suitable alkoxy radicals include, for example, methoxy, ethoxy, benzyloxy, t-butoxy, etc. A related term is "aryloxy" where Z$^1$ is selected from the group consisting of aryl, substituted aryl, heteroaryl, substituted heteroaryl, and combinations thereof. Examples of suitable aryloxy radicals include phenoxy, substituted phenoxy, 2-pyridinoxy, 8-quinalinoxy and the like.

As used herein the term "silyl" refers to the —SiZ$^1$Z$^2$Z$^3$ radical, where each of Z$^1$, Z$^2$, and Z$^3$ is independently selected from the group consisting of hydrogen, alkyl, substituted alkyl, cycloalkyl, heterocycloalkyl, heterocyclic, aryl, substituted aryl, heteroaryl, substituted heteroaryl, alkoxy, aryloxy, amino, silyl and combinations thereof.

As used herein the term "boryl" refers to the —BZ$^1$Z$^2$ group, where each of Z$^1$ and Z$^2$ is independently selected from the group consisting of hydrogen, alkyl, substituted alkyl, cycloalkyl, heterocycloalkyl, heterocyclic, aryl, substituted aryl, heteroaryl, substituted heteroaryl, alkoxy, aryloxy, amino, silyl and combinations thereof.

As used herein, the term "phosphino" refers to the group —PZ$^1$Z$^2$, where each of Z$^1$ and Z$^2$ is independently selected from the group consisting of hydrogen, substituted or unsubstituted alkyl, cycloalkyl, heterocycloalkyl, heterocyclic, aryl, substituted aryl, heteroaryl, silyl, alkoxy, aryloxy, amino and combinations thereof.

As used herein, the term "phosphine" refers to the group: PZ$^1$Z$^2$Z$^3$, where each of Z$^1$, Z$^3$and Z$^2$ is independently selected from the group consisting of hydrogen, substituted or unsubstituted alkyl, cycloalkyl, heterocycloalkyl, heterocyclic, aryl, substituted aryl, heteroaryl, silyl, alkoxy, aryloxy, amino and combinations thereof.

The term "amino" is used herein to refer to the group —NZ$^1$Z$^2$, where each of Z$^1$ and Z$^2$ is independently selected from the group consisting of hydrogen, alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, silyl and combinations thereof.

The term "amine" is used herein to refer to the group: NZ$^1$Z$^2$Z$^3$, where each of Z$^1$, Z$^2$ and Z$^2$ is independently selected from the group consisting of hydrogen, alkyl, substituted alkyl, cycloalkyl, substituted cycloalkyl, heterocycloalkyl, substituted heterocycloalkyl, aryl (including pyridines), substituted aryl, heteroaryl, substituted heteroaryl, alkoxy, aryloxy, silyl and combinations thereof.

The term "thio" is used herein to refer to the group —SZ$^1$, where Z$^1$ is selected from the group consisting of hydrogen, alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, silyl and combinations thereof.

The term "seleno" is used herein to refer to the group —SeZ$^1$, where Z$^1$ is selected from the group consisting of hydrogen, alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, silyl and combinations thereof.

The term "saturated" refers to lack of double and triple bonds between atoms of a radical group such as ethyl, cyclohexyl, pyrrolidinyl, and the like.

The term "unsaturated" refers to the presence one or more double and triple bonds between atoms of a radical group such as vinyl, acetylide, oxazolinyl, cyclohexenyl, acetyl and the like.

Ligands

Suitable ligands useful in this invention can be characterized broadly as monoanionic ligands having an amine and a heteroaryl or substituted heteroaryl group. These ligands may be characterized by the following general formula:

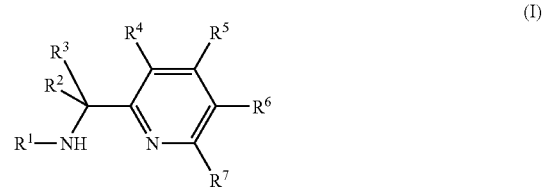

(I)

wherein R$^1$ is selected from the group consisting alkyl, substituted alkyl, cycloalkyl, substituted cycloalkyl, heteroalkyl, substituted heteroalkyl, heterocycloalkyl, substituted hetercycloalkyl, aryl, substituted aryl, heteroaryl, substituted heteroaryl and combinations thereof;

R$^2$, R$^3$ R$^4$, R$^5$, R$^6$ and R$^7$ are independently selected from the group consisting of hydrogen, alkyl, substituted alkyl, cycloalkyl, substituted cycloalkyl, heteroalkyl, substituted heteroalkyl, heterocycloalkyl, substituted hetercycloalkyl, aryl, substituted aryl, heteroaryl, substituted heteroaryl, alkoxyl, aryloxyl, silyl, boryl, phosphino, amino, thio, seleno, halide, nitro, and combinations thereof. One or more R groups may be joined to one or more other R groups to form one or more ring structures.

In certain embodiments, R$^1$ is a ring having from 4-8 atoms in the ring generally selected from the group consisting of substituted cycloalkyl, substituted heterocycloalkyl, substituted aryl and substituted heteroaryl, such that R$^1$ may be characterized by the general formula:

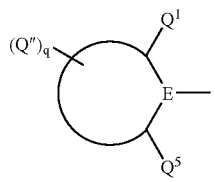

where Q$^1$ and Q$^5$ are substituents on the ring ortho to atom E, with E being selected from the group consisting of carbon and nitrogen and with at least one of Q$^1$ or Q$^5$ being bulky (defined as having at least 2 atoms). Q"$_q$ represents additional possible substituents on the ring, with q being 1, 2, 3, 4 or 5 and Q" being selected from the group consisting of hydrogen, alkyl, substituted alkyl, cycloalkyl, substituted cycloalkyl, heteroalkyl, substituted heteroalkyl, heterocycloalkyl, substituted hetercycloalkyl, aryl, substituted aryl, heteroaryl, substituted heteroaryl, alkoxyl, aryloxyl, silyl, boryl, phosphino, amino, thio, seleno, halide, nitro, and combinations thereof.

In more specific embodiments, $R^1$ is selected from the group consisting of aryl, substituted aryl, heteroaryl, substituted heteroaryl and combinations thereof.

In certain more specific embodiments, the ligands in this invention may be characterized by the following general formula:

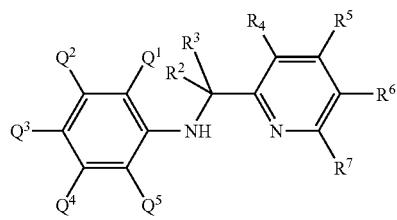

(II)

wherein $Q^2$, $Q^3$ and $Q^4$ are independently selected from the group consisting of hydrogen, alkyl, substituted alkyl, cycloalkyl, substituted cycloalkyl, heteroalkyl, substituted heteroalkyl, heterocycloalkyl, substituted hetercycloalkyl, aryl, substituted aryl, heteroaryl, substituted heteroaryl, alkoxyl, aryloxyl, silyl, boryl, phosphino, amino, thio, seleno, nitro, and combinations thereof; and $Q^1$ and $Q^5$ are selected from the group consisting of alkyl, substituted alkyl, cycloalkyl, substituted cycloalkyl, aryl, substituted aryl. One or more Q or R groups may be joined to one or more other Q or R groups to form one or more ring structures.

In some other embodiments, it is preferred that $R^2$ is hydrogen, providing a chiral center. In these embodiments, $R^3$ is selected preferably from the group consisting of aryl, substituted aryl, heteroaryl, substituted heteroaryl, primary and secondary alkyl groups, and —$PY_2$ where Y is selected from the group consisting of aryl, substituted aryl, heteroaryl, and substituted heteroaryl.

These more specific embodiments can be combined together. And, specific ligands useful in this invention include:

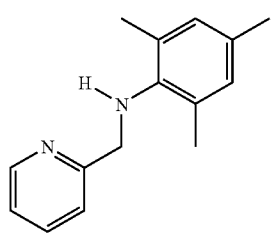

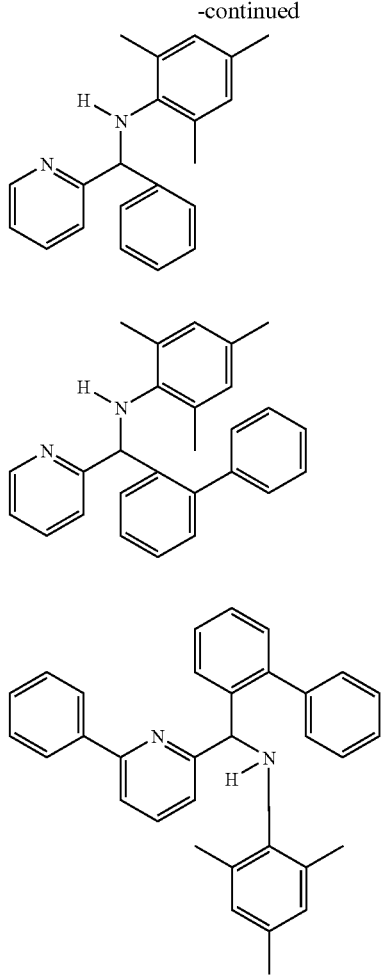

The ligands of the invention may be prepared using known procedures. See, for example, Advanced Organic Chemistry, March, Wiley, New York 1992 (4$^{th}$ Ed.). Specifically, the ligands of the invention may be prepared using the two step procedure outlined in Scheme 1.

Scheme 1

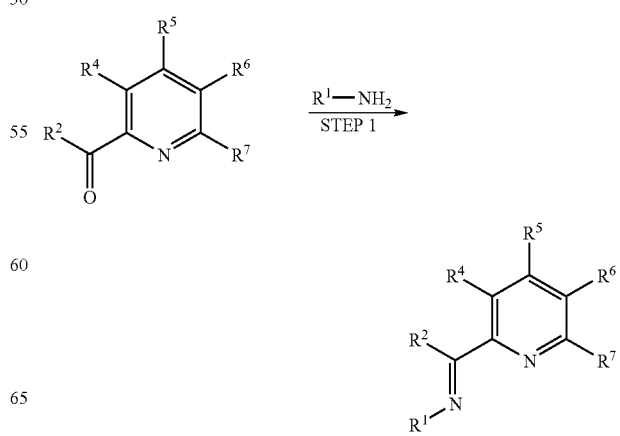

-continued

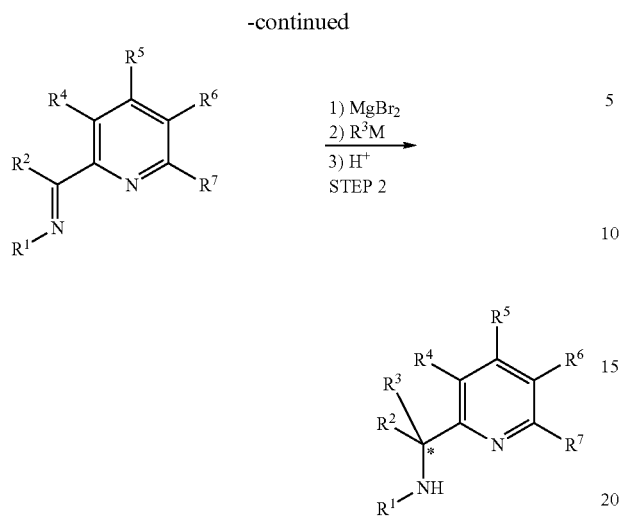

In Scheme 1, the * represents a chiral center when $R^2$ and $R^3$ are not identical; also, the R groups have the same definitions as above. Generally, $R^3M$ is a nucleophile such as an alkylating or arylating or hydrogenating reagent and M is a metal such as a main group metal, or a metalloid such as boron. The alkylating, arylating or hydrogenating reagent may be a Grignard, alkyl, aryl-lithium or borohydride reagent. Scheme 1, step 2 first employs the use of complexing reagent. Preferably, as in the case of Scheme 1, magnesium. bromide is used as the complexing reagent. The role of the complexing reagent is to direct the nucleophile, $R^3M$, selectively to the imine carbon. Where the presence of functional groups impede this synthetic approach, alternative synthetic strategies may be employed. For instance, ligands where $R^3$=phosphino can be prepared in accordance with the teachings of U.S. Pat. No. 6,034,240 and U.S. Pat. No. 6,043,363. In addition, tetra-alkyltitanium compounds or tetra-substituted alkyltitanium compounds or tetra-aryltitanium compounds or tetra-substituted aryltitanium compounds may be employed in step 2, in accordance with the teachings of U.S. Pat. No. 6,103,657, which is incorporated herein by reference.

For the case when $R^2$ and $R^3$ are both hydrogen, the second step in the reaction sequence is a reduction reaction using sodiumtriacetozyborohydride (Na(OAc)$_3$BH) in THF for 1-3 days followed by aq. NH$_4$Cl quench.

Scheme 2 further describes a synthesis process:

Scheme 2

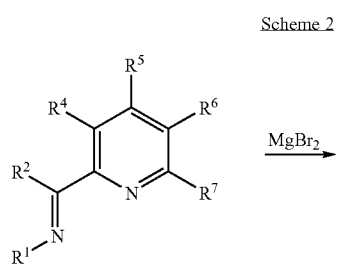

-continued

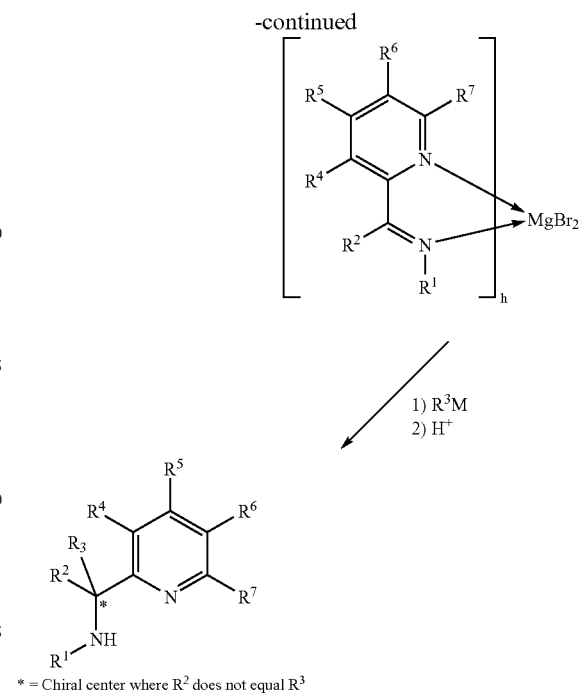

* = Chiral center where $R^2$ does not equal $R^3$

In scheme 2, h=1 or 2 and the bromine ions may or may not be bound to the magnesium. Upon complexation to the complexing reagent the imine nitrogen is rendered less electrophillic. The effect of the complexation is therefore to guide the subsequent nucleophilic attack by $R^3M$ to the imine carbon. Thus complexation may lead to a more selective reaction that may increase the yield of the desired ancillary ligands. Using this technique, selectivity is generally greater than about 50%, more preferably greater than about 70% and even more preferably greater than about 80%. Complexation may be particularly useful for the preparation of arrays of ancillary ligands of the type disclosed in the invention, where $R^3$ is a variable in the preparation of the ancillary ligand array. As shown in Scheme 2 by the *, where $R^2$ and $R^3$ are different, this approach also leads to the formation of a chiral center on the ancillary ligands of the invention. Ancillary ligands that possess chirality may be important in certain olefin polymerization reactions, particularly those that lead to a stereospecific polymer, see "Stereospecific Olefin Polymerization with Chiral Metallocene Catalysts", Brintzinger, et al., *Angew. Chem. Int. Ed. Engl.*, 1995, Vol. 34, pp. 1143-1170, and the references therein; Bercaw et al., *J. Am. Chem. Soc.*, 1999, Vol. 121, 564-573; and Bercaw et al., *J. Am. Chem. Soc.*, 1996, Vol. 118, 11988-11989; each of which is incorporated herein by reference.

Compositions

Once the desired ligand is formed, it may be combined with a titanium atom, ion, compound or other titanium precursor compound. In some applications, the ligands of this invention will be combined with such a titanium compound or precursor and the product of such combination is not determined, if a product forms. For example, the ligand may be added to a reaction vessel at the same time as the titanium or titanium precursor compound along with the reactants, activators, scavengers, etc. Additionally, the ligand can be modified prior to addition to or after the addition of the metal precursor, e.g. through a deprotonation reaction or some other modification.

The metal precursor compounds may be characterized by the general formula $Ti(L)_n$ where L is independently selected from the group consisting of halide (F, Cl, Br, I), alkyl, substituted alkyl, cycloalkyl, substituted cycloalkyl, heteroalkyl, substituted heteroalkyl, heterocycloalkyl, substituted heterocycloalkyl, aryl, substituted aryl, heteroaryl, substituted heteroaryl, alkoxy, aryloxy, hydroxy, boryl, silyl, amino, amine, hydrido, allyl, diene, seleno, phosphino, phosphine, ether, thioether, carboxylates, thio, 1,3-dionates, oxalates, carbonates, nitrates, sulphates, and combinations thereof. n is 1, 2, 3, 4, 5, or 6. The titanium precursors may be monomeric, dimeric or higher orders thereof. It is well known that titanium metal typically contains some amount of impurity of zirconium. Thus, this invention uses as pure titanium as is commercially reasonable.

Specific examples of suitable titanium precursors include, but are not limited to $TiCl_4$, $Ti(CH_2Ph)_4$, $Ti(CH_2CMe_3)_4$, $Ti(CH_2SiMe_3)_4$, $Ti(CH_2Ph)_3Cl$, $Ti(CH_2CMe_3)_3Cl$, $Ti(CH_2SiMe_3)_3Cl$, $Ti(CH_2Ph)_2Cl_2$, $Ti(CH_2CMe_3)_2Cl_2$, $Ti(CH_2SiMe_3)_2Cl_2$, $Ti(NMe_2)_4$, $Ti(NEt_2)_4$, $Ti(NMe_2)_2Cl_2$, $Ti(NEt_2)_2Cl_2$, and $Ti(N(SiMe_3)_2)_2Cl_2$, $Ti(OCH_2CH_3)_4$, $Ti(OCH(CH_3)_2)_4$, $TiCl(OCH(CH_3)_2)_3$, $Ti(OCH_2CH_2CH_3)_4$, $Ti(OEt)_4$, $Ti(N(SiMe_3)_2)_3$, $TiCl_3$. Lewis base adducts of these examples are also suitable as titanium precursors, for example, ethers, amines, thioethers, phosphines and the like are suitable as Lewis bases. Examples of suitable Lewis base adducts of titanium precursors include, but are not limited to $TiCl_3(THF)_3$, or $TiCl_4(NH_3)_2$.

The ligand may be mixed with a suitable metal precursor compound prior to or simultaneously with allowing the mixture to be contacted with the reactants (e.g., monomers). In this context, the ligand to metal precursor compound ratio is in the range of about 0.01:1 to about 100:1, more preferably in the range of about 0.1:1 to about 10:1.

Metal-Ligand Complexes

When the ligand is mixed with the metal precursor compound, a metal-ligand complex may be formed, which may be a catalyst or may need to be activated to be a catalyst. Depending on the substituents chosen for the ligand prior to reaction with the metal precursor compound, the metal-ligand complexes may be characterized by the following general formula:

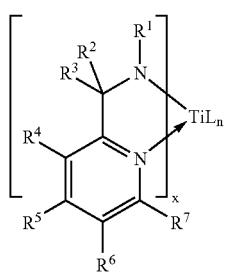

(III)

wherein $R^1$, $R^2$, $R^3$, $R^4$, $R^5$, $R^6$, $R^7$, and L are as defined previously; and x is 1 or 2 and n is 1, 2, 3 or 4. In one preferred embodiment for titanium in the +4 oxidation state x=1 and n=3. In other embodiments, titanium may be in the +3 oxidation state, in which case one preferred embodiment is when x=1 and n=2. Additionally, Lewis base adducts of these metal-ligand complexes are also within the scope of the invention, for example, ethers, amines, thioethers, phosphines and the like are suitable as Lewis bases.

In certain embodiments, $R^1$ is a ring having from 4-8 atoms in the ring generally selected from the group consisting of substituted cycloalkyl, substituted heterocycloalkyl, substituted aryl and substituted heteroaryl, such that $R^1$ may be characterized by the general formula:

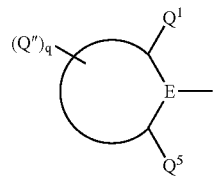

where $Q^1$ and $Q^5$ are substituents on the ring ortho to atom E, with E being selected from the group consisting of carbon and nitrogen and with at least one of $Q^1$ or $Q^5$ being bulky (defined as having at least 2 atoms). $Q'''^q$ represents additional possible substituents on the ring, with q being 1, 2, 3, 4 or 5 and Q'' being selected from the group consisting of hydrogen, alkyl, substituted alkyl, cycloalkyl, substituted cycloalkyl, heteroalkyl, substituted heteroalkyl, heterocycloalkyl, substituted hetercycloalkyl, aryl, substituted aryl, heteroaryl, substituted heteroaryl, alkoxyl, aryloxyl, silyl, boryl, phosphino, amino, thio, seleno, halide, nitro, and combinations thereof.

More specifically, the metal-ligand complexes of this invention may be characterized by the general formula:

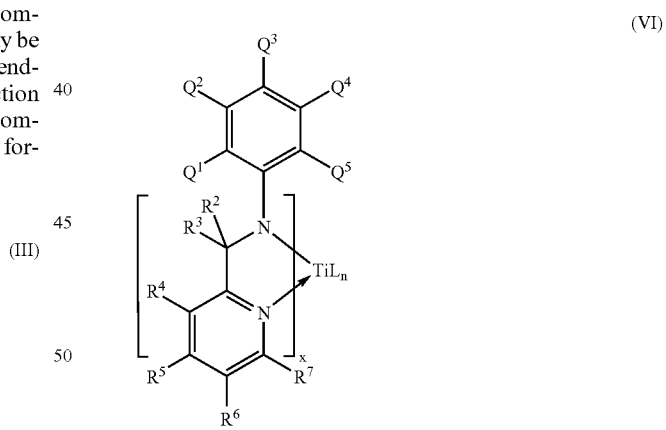

(VI)

wherein the variables are generally defined above.

In general, one or more L can be joined to one or more R or Q groups, or to one or more other L groups to form ring structures. Furthermore in preferred embodiments, L is selected from the group consisting of alkyl, substituted alkyl, aryl, substituted aryl or amino.

The more specific embodiments of these metal complexes are explained above with regard to the specifics described for the ligands and metal precursors. Within formulas III and IV, specific examples of metal-ligand complexes include, but are not limited to:

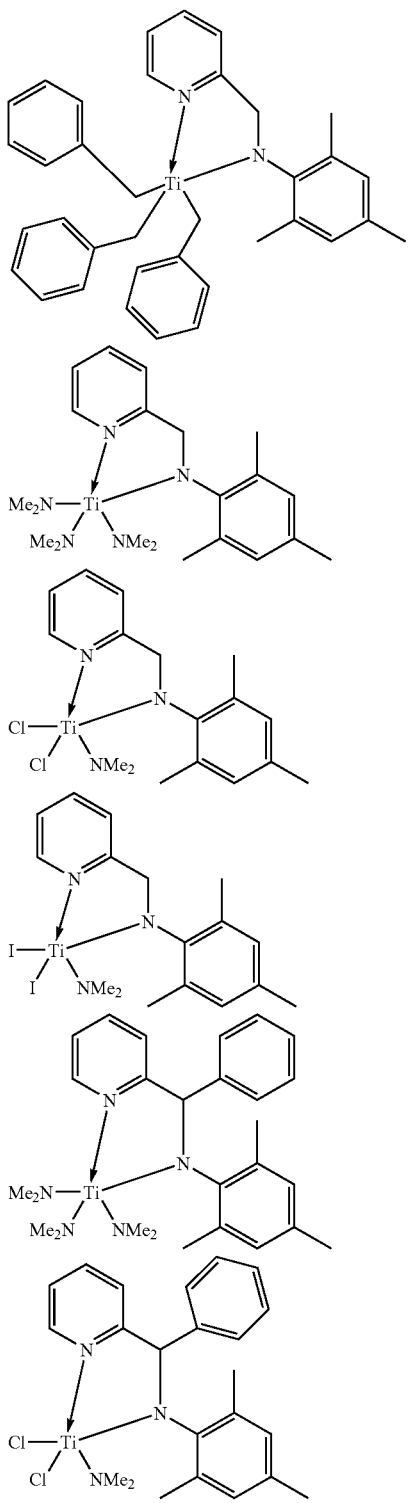

Various references disclose metal complexes that may appear to be similar; see for example, U.S. Pat. No. 6,103,657 and U.S. Pat. No. 5,637,660, both of which are incorporated herein by reference for all purposes. However, certain embodiments of the invention herein provide unexpectedly improved polymerization performance (e.g., higher activity and/or higher polymerization temperatures and/or higher comonomer incorporation) relative to the embodiments disclosed in those references. In particular, as shown in certain of the examples herein, the titanium metal catalysts show superior performance with respect to incorporation of styrene into an ethylene/styrene copolymer.

The ligands, complexes or catalysts may be supported on an organic or inorganic support. Suitable supports include silicas, aluminas, clays, zeolites, magnesium chloride, polyethyleneglycols, polystyrenes, polyesters, polyamides, peptides and the like. Polymeric supports may be cross-linked or not. Similarly, the ligands, complexes or catalysts may be supported on similar supports known to those of skill in the art. In addition, the catalysts of this invention may be combined with other catalysts in a single reactor and/or employed in a series of reactors (parallel or serial) in order to form blends of polymer products.

Polymerization Activators/Additives

The metal-ligand complexes and compositions are active catalysts typically in combination with a suitable activator, combination of activators, activating technique or activating package, although some of the ligand-metal complexes may be active without an activator or activating technique. Broadly, the activator(s) may comprise alumoxanes, Lewis acids, Bronsted acids, compatible non-interfering activators and combinations of the foregoing. These types of activators have been taught for use with different compositions or metal complexes in the following references, which are hereby incorporated by reference in their entirety: U.S. Pat Nos. 5,599,761, 5,616,664, 5,453,410, 5,153,157, 5,064,802, and EP-A-277,004. In particular, ionic or ion forming activators are preferred.

Suitable ion forming compounds useful as an activator in one embodiment of the present invention comprise a cation that is a Bronsted acid capable of donating a proton, and an inert, compatible, non-interfering, anion, $A^-$. Preferred anions are those containing a single coordination complex comprising a charge-bearing metal or metalloid core. Mechanistically, said anion should be sufficiently labile to be displaced by olefinic, diolefinic and unsaturated compounds or other neutral Lewis bases such as ethers or nitriles. Suitable metals include, but are not limited to, aluminum, gold and platinum. Suitable metalloids include, but are not limited to, boron, phosphorus, and silicon. Compounds containing anions that comprise coordination complexes containing a single metal or metalloid atom are, of course, well known and many, particularly such compounds containing a single boron atom in the anion portion, are available commercially.

Preferably such activators may be represented by the following general formula:

$$(L^*-H)_d^+ (A^{d-})$$

wherein, $L^*$ is a neutral Lewis base; $(L^*-H)^+$ is a Bronsted acid; $A^{d-}$ is a non-interfering, compatible anion having a charge of d−, and d is an integer from 1 to 3. More preferably $A^{d-}$ corresponds to the formula: $[M'^{3+} Q_h]^{d-}$ wherein h is an integer from 4 to 6; h−3=d; M' is an element selected from Group 13 of the Periodic Table of the Elements; and Q is independently selected from the group consisting of hydride, dialkylamido, halide, alkoxide, aryloxide, hydrocarbyl, and substituted-hydrocarbyl radicals (including halosubstituted hydrocarbyl, such as perhalogenated hydrocarbyl radicals), said Q having up to 20 carbons. In a more preferred embodiment, d is one, i.e., the counter ion has a single negative charge and corresponds to the formula $A^-$.

Activators comprising boron or aluminum which are particularly useful in the preparation of catalysts of this invention may be represented by the following general formula:

[L*-H]⁺[JQ₄]⁻ wherein: L* is as previously defined; J is boron or aluminum; and Q is a fluorinated $C_{1-20}$ hydrocarbyl group. Most preferably, Q is independently selected from the group selected from the group consisting of fluorinated aryl group, especially, a pentafluorophenyl group-(i.e., a $C_6F_5$ group) or a 3,5-bis($CF_3$)$_2C_6H_3$ group. Illustrative, but not limiting, examples of boron compounds which may be used as an activating cocatalyst in the preparation of the improved catalysts of this invention are tri-substituted ammonium salts such as: trimethylammonium tetraphenylborate, triethylammonium tetraphenylborate, tripropylammonium tetraphenylborate, tri(n-butyl)ammonium tetraphenylborate, tri(t-butyl) ammonium tetraphenylborate, N,N-dimethylanilinium tetraphenylborate, N,N-diethylanilinium tetraphenylborate, N,N-dimethylanilinium tetra-(3,5-bis(trifluoromethyl)phenyl)borate, N,N-dimethyl-(2,4,6-trimethylanilinium)tetraphenylborate, trimethylammonium tetrakis(pentafluorophenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(secbutyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium)tetrakis(pentafluorophenyl)borate, trimethylammonium tetrakis-(2,3,4,6-tetrafluorophenylborate and N,N-dimethylanilinium tetrakis(2,3,4,6-tetrafluorophenyl)borate; dialkyl ammonium salts such as: di-(i-propyl)ammonium tetrakis(pentafluorophenyl)borate, and dicyclohexylammonium tetrakis(pentafluorophenyl)borate; and tri-substituted phosphonium salts such as: triphenylphospnonium tetrakis(pentafluorophenyl)borate, tri(o-tolyl)phosphonium tetrakis(pentafluorophenyl)borate, and tri(2,6-dimethylphenyl)phosphonium tetrakis(pentafluorophenyl)borate; and N,N-dimethylanilinium tetrakis(3,5-bis(trifluoromethyl)phenyl)borate. Preferred [L*-H]⁺cations are N,N-dimethylanilinium and tributylammonium. Preferred anions are tetrakis(3,5-bis(trifluoromethyl)phenyl)borate and tetrakis(pentafluorophenyl)borate. In some embodiments, the most preferred activator is PhNMe₂H⁺B($C_6F_5$)₄⁻.

Other suitable ion forming activators comprise a salt of a cationic oxidizing agent and a non-interfering, compatible anion represented by the formula:

$(Ox^{e+})_d(A^{d-})_e$ wherein: $Ox^{e+}$ is a cationic oxidizing agent having a charge of e+; e is an integer from 1 to 3; and $A^{d-}$, and d are as previously defined. Examples of cationic oxidizing agents include: ferrocenium, hydrocarbyl-substituted ferrocenium, Ag⁺, or Pb⁺². Preferred embodiments of $A^{d-}$ are those anions previously defined with respect to the Bronsted acid containing activating cocatalysts, especially tetrakis(pentafluorophenyl) borate.

Another suitable ion forming, activating cocatalyst comprises a compound that is a salt of a carbenium ion or silyl cation and a non-interfering, compatible anion represented by the formula:

⁺A⁻ wherein: ⁺ is a $C_{1-100}$ carbenium ion or silyl cation; and A⁻ is as previously defined. A preferred carbenium ion is the trityl cation, i.e. triphenylcarbenium. The silyl cation may be characterized by the formula $Z^1Z^2Z^3Si^+$ cation, where each of $Z^1$, $Z^2$, and $Z^3$ is independently selected from the group consisting of alkyl, substituted alkyl, cycloalkyl, heterocycloalkyl, heterocyclic, aryl, substituted aryl, heteroaryl, substituted heteroaryl and combinations thereof.

Other suitable activating cocatalysts comprise a compound that is a salt, which is represented by the formula $(A^{*+a})_b(Z^*J^*_j)^{-c}_d$ wherein A* is a cation of charge +a; Z* is an anion group of from 1 to 50, preferably 1 to 30 atoms, not counting hydrogen atoms, further containing two or more Lewis base sites; J* independently each occurrence is a Lewis acid coordinated to at least one Lewis base site of Z*, and optionally two or more such J* groups may be joined together in a moiety having multiple Lewis acidic functionality; j is a number form 2 to 12; and a, b, c, and d are integers from 1 to 3, with the proviso that a×b is equal to c×d. See, WO 99/42467, which is incorporated herein by reference. In other embodiments, the anion portion of these activating cocatalysts may be characterized by the formula $((C_6F_5)_3M''''-LN-M'''' (C_6F_5)_3)^-$ where M'''' is boron or aluminum and LN is a linking group, which is preferably selected from the group consisting of cyanide, azide, dicyanamide and imidazolide. The cation portion is preferably a quaternary amine. See, e.g., LaPointe et al., *J. Am. Chem. Soc.* 2000, 122, 9560-9561, which is incorporated herein by reference.

In addition, suitable activators include Lewis acids, such as those selected from the group consisting of tris(aryl)boranes, tris(substituted aryl)boranes, tris(aryl)alanes, tris(substituted aryl)alanes, including activators such as tris(pentafluorophenyl)borane. Other useful ion forming Lewis acids include those having two or more Lewis acidic sites, such as those described in WO 99/06413 or Piers, et al. "New Bifunctional Perfluoroaryl Boranes: Synthesis and Reactivity of the ortho-Phenylene-Bridged Diboranes 1,2-[B($C_6F_5$)₂]₂$C_6X_4$ (X=H, F)", *J. Am. Chem. Soc.*, 1999, 121, 3244-3245, both of which are incorporated herein by reference. Other useful Lewis acids will be evident to those of skill in the art. In general, the group of Lewis acid activators are within the group of ion forming activators (although exceptions to this general rule can be found) and the group tends to exclude the group 13 reagents listed below. Combinations of ion forming activators may be used.

Other general activators or compounds useful in a polymerization reaction may be used. These compounds may be activators in some contexts, but may also serve other functions in the polymerization system, such as alkylating a metal center or scavenging impurities. These compounds are within the general definition of "activator," but are not considered herein to be ion forming activators. These compounds include a group 13 reagent that may be characterized by the formula $G^{13}R'_{3-p}D_p$ where $G^{13}$ is selected from the group consisting of B, Al, Ga, In and combinations thereof, p is 0, 1 or 2, each R' is independently selected from the group consisting of alkyl, substituted alkyl, cycloalkyl, heterocycloalkyl, heterocyclic and combinations thereof, and each D is independently selected from the group consisting of halide, hydride, alkoxy, aryloxy, amino, thio, phosphino and combinations thereof. In other embodiments, the group 13 activator is an oligomeric or polymeric alumoxane compound, such as methylalumoxane and the known modifications thereof. In other embodiments, a divalent metal reagent may be used that is defined by the general formula $M'R'_{2-p'}D_{p'}$ and p' is 0 or 1 in this embodiment and R' and D are as defined above. M' is the metal and is selected from the group consisting of Mg, Ca, Sr, Ba, Zn, Cd and combinations thereof. In still other embodiments, an alkali metal reagent may be used that is defined by the general formula M"R' and in this embodiment R' is as defined above. M" is the alkali metal and is selected from the group consisting of Li, Na, K, Rb, Cs and combinations thereof. Additionally, hydrogen and/or silanes may be used in the catalytic composition or added to the polymerization system. Silanes may be characterized by the formula $SiR'_{4-q}D_q$ where R' is defined as above, q is 1, 2, 3 or 4 and D is as defined above, with the proviso that there is at least one D that is a hydride.

The molar ratio of metal: activator (whether a composition or complex is employed as a catalyst) employed preferably ranges from 1:10,000 to 100:1, more preferably from 1:5000 to 10:1, most preferably from 1:10 to 1:1. In a preferred embodiment of the invention mixtures of the above compounds are used, particularly a combination of a group 13 reagent and an ion-forming activator. The molar ratio of group 13 reagent to ion-forming activator is preferably from 1:10,000 to 1000:1, more preferably from 1:5000 to 100:1, most preferably from 1:100 to 100:1. In a preferred embodiment, the ion forming activators are combined with a tri-alkyl aluminum, specifically trimethylaluminum, triethylaluminum, tri-n-octylaluminum, or triisobutylaluminum or with a di-alkyl aluminum hydride such as di-isobutyl aluminum hydride. A most preferred combination is about 1 equivalent of N,N-dimethylanilinium tetrakis(pentafluorophenyl) borate, and 10-30 equivalents of tri(isobutyl)aluminum.

In other applications, the ligand will be mixed with a suitable metal precursor compound prior to or simultaneous with allowing the mixture to be contacted to the reactants. When the ligand is mixed with the metal precursor compound, a metal-ligand complex may be formed, which may be a catalyst. In connection with the metal-ligand complex and depending on the ligand or ligahds chosen, the metal-ligand complex may take the form of dimers, trimers or higher orders thereof or there may be two or more metal atoms that are bridged by one or more ligands. Furthermore, two or more ligands may coordinate with a single metal atom. The exact nature of the metal-ligand complex(es) or compound(s) formed depends on the chemistry of the ligand and the method of combining the metal precursor and ligand, such that a distribution of metal-ligand complexes may form with the number of ligands bound to the metal being greater or less than the number of equivalents of ligands added relative to an equivalent of metal precursor.

Monomers/Polymers

The compositions, complexes and/or catalysts of this invention are particularly effective at copolymerizing ethylene with styrene monomers. The styrene monomers may be unsubstituted or substituted at one or more positions on the aryl ring. The ethylene-styrene copolymers can have high styrene incorporation and high molecular weight.

It has been found that the catalysts of the present invention are also active for the polymerization of certain other monomers, particularly α-olefins. Thus, the catalysts of the present invention may provide higher comonomer incorporation for copolymers of ethylene and co-monomers having three or more carbon atoms.

Novel polymers, copolymers or interpolymers may be formed having unique physical and/or melt flow properties. Such novel polymers can be employed alone or with other polymers in a blend to form products that may be molded, cast, extruded or spun. End uses for the polymers made with the catalysts of this invention include films for packaging, trash bags, bottles, containers, foams, coatings, insulating devices and household items. Also, such functionalized polymers are usefuil as solid supports for organometallic or chemical synthesis processes.

Polymerization can be carried out in the Ziegler-Natta or Kaminsky-Sinn methodology, including temperatures of from −100° C. to 300° C. and pressures from atmospheric to 3000 atmospheres. Suspension, solution, slurry, gas phase or high-pressure polymerization processes may be employed with the catalysts and compounds of this invention. Such processes can be run in a batch, semi-batch or continuous mode. Examples of such processes are well known in the art. A support for the catalyst may be employed, which may be inorganic (such as alumina, magnesium chloride or silica) or organic (such as a polymer or cross-linked polymer). Methods for the preparation of supported catalysts are known in the art. Gas phase, slurry, suspension, and high-pressure processes as known to those skilled in the art may also be used with supported catalysts of the invention.

Suitable solvents for polymerization are non-coordinating, inert liquids. Examples include straight and branched-chain hydrocarbons such as isobutane, butane, pentane, isopentane, hexane, isohexane, heptane, octane, Isopar-E® and mixtures thereof; cyclic and alicyclic hydrocarbons such as cyclohexane, cycloheptane, methylcyclohexane, methylcycloheptane, and mixtures thereof, perhalogenated hydrocarbons such as perfluorinated $C_{4-10}$ alkanes, chlorobenzene, and aromatic and alkylsubstituted aromatic compounds such as benzene, toluene, mesitylene, and xylene. Suitable solvents also include liquid olefins which may act as monomers or comonomers including ethylene, propylene, 1-butene, butadiene, cyclopentene, 1-hexene, 1-pentene, 3-methyl-1-pentene, 4-methyl-1-pentene, 1,4-hexadiene, 1-octene, 1-decene, isobutylene, styrene, divinylbenzene, allylbenzene, vinyltoluene (including all isomers alone or in admixture), vinyl chloride, acrylonitrile, acrylates, vinyl acetate, methacrylates, 4-vinylcyclohexene, and vinylcyclohexane. Mixtures of the foregoing are also suitable.

Other additives that are useful in a polymerization reaction may be employed, such as scavengers, promoters, modifiers and/or chain transfer agents, such as hydrogen, aluminum alkyls and/or silanes.

As discussed herein, catalytic performance can be determined a number of different ways, as those of skill in the art will appreciate. Catalytic performance can be determined by the yield of polymer obtained per mole of metal complex, which in some contexts may be considered to be activity.

Another measure of catalyst polymerization performance is co-monomer incorporation. As is well known in the art, many ethylene copolymers are prepared using ethylene and at least one other monomer. These copolymers or higher order polymers in some applications require higher amounts of additional co-monomer(s) than have been practical with known catalysts. Since ethylene tends to be the most reactive monomer, obtaining higher co-monomer incorporations is a benefit that is examined for polymerization catalysts. This invention demonstrates higher incorporation of styrene. As shown herein, the ethylene/styrene copolymers obtained from the polymerization reaction also have high Mw, which is also desirable.

The results of ethylene-styrene copolymerizations using ancillary ligands of the invention in combination with titanium precursors or with isolated titanium metal complexes are surprising. The results illustrate that certain combinations are more productive in the copolymerization of ethylene with styrene, for example, to produce copolymers with a higher mol % styrene incorporation, when compared with other metal centers, such as zirconium or hafnium, under similar conditions. Incorporation of high levels of styrene (e.g., >10 mol %) into ethylene-styrene copolymers under solution polymerization conditions was observed as compared to hafilium complexes of the same ligands which incorporated lower levels of styrene (<5 mol %) under the same conditions.

Also, these titanium complexes of substituted pyridylamine ligands of this invention show surprising thermal robustness, compared to many other non-cyclopentadienyl titanium-based olefin polymerization catalysts.

Combinatorial Methodology

The ligands, metal-ligand complexes and compositions of this invention can be prepared-and tested for catalytic activity in one or more of the above reactions in a combinatorial fashion. Combinatorial chemistry generally involves the parallel or rapid serial synthesis and/or screening or characterization of compounds and compositions of matter. U.S. Pat. No. Nos. 5,985,356, 6,030,917 and WO 98/03521, all of which are incorporated herein by reference, generally disclose combinatorial methods. In this regard, the ligands, metal-ligand complexes or compositions may be prepared and/or tested in rapid serial and/or parallel fashion, e.g., in an array format. When prepared in an array format, ligands, metal-ligand complexes or compositions may be take the form of an array comprising a plurality of compounds wherein each compound can be characterized by any of the above general formulas (i.e. I, II, III or IV). An array of ligands may be synthesized using the procedures outlined previously. The array may also be of metal precursor compounds, the metal-ligand complexes or compositions characterized by the previously described formulae and/or description. Typically, each member of the array will have differences so that, for example, a ligand or activator or metal precursor or R group in a first region of the array may be different than the ligand or activator or metal precursor or R group in a second region of the array. Other variables may also differ from region to region in the array.

In such a combinatorial array, typically each of the plurality of compositions or complexes has a different composition or stoichiometry, and typically each composition or complex is at a selected region on a substrate such that each compound is isolated from the other compositions or complexes. This isolation can take many forms, typically depending on the substrate used. If a flat substrate is used, there may simply be sufficient space between regions so that there cannot be interdiffusion between compositions or complexes. As another example, the substrate can be a microtiter or similar plate having wells so that each composition or complex is in a region separated from other compounds in other regions by a physical barrier. The array may also comprise a parallel reactor or testing chamber.

The array typically comprises at least 8 compounds, complexes or compositions each having a different chemical formula, meaning that there must be at least one different atom or bond differentiating the members in the array or different ratios of the components referred to herein (with components referring to ligands, metal precursors, activators, group 13 reagents, solvents, monomers, supports, etc.). In other embodiments, there are at least 20 compounds, complexes or compositions on or in the substrate each having a different chemical formula. In still other embodiments, there are at least 40 or 90 or 124 compounds, complexes or compositions on or in the substrate each having a different chemical formula. Because of the manner of forming combinatorial arrays, it may be that each compound, complex or composition may not be worked-up, purified or isolated, and for example, may contain reaction by-products or impurities or unreacted starting materials.

The catalytic performance of the compounds, complexes or compositions of this invention can be tested in a combinatorial or high throughput fashion. Polymerizations can also be performed in a combinatorial fashion, see, e.g., U.S. patent applications Ser. No. 09/239,223, filed Jan. 29, 1999; Ser. No. 09/239,223, filed Jan. 29, 1999; and WO 00/09255 and U.S. Pat. No. 6,306,658, each of which is herein incorporated by reference.

EXAMPLES

General: All reactions were performed under a purified argon or nitrogen atmosphere in a Vacuum Atmospheres glove box. All solvents used-were of the anhydrous, de-oxygenated and purified according to known techniques. All ligands and metal precursors were prepared according to procedures known to those of skill in the art, e.g., under inert conditions, etc. Ethylene/styrene and ethylene/1-octene copolymerizations were carried out in a parallel pressure reactor, which is fully described in pending U.S. patent applications Ser. No. 09/177,170, filed Oct. 22, 1998, Ser. No. 09/239,223, filed Jan. 29, 1999 and U.S. Pat. No. 6,306,658 and WO 00/09255, each of which is incorporated herein by reference.

The ratio of styrene to ethylene incorporated in the-polymer products, represented as the mol % of styrene incorporated in the polymer (mol % incorporated styrene) was determined using FTIR spectroscopy, using a Partial Least Squares (PLS) analysis method. FTIR was performed on a Bruker Equinox 55+IR Scope II in reflection mode using a Pike MappIR accessory with 16 scans.

The ratio of styrene to ethylene incorporated in the polymer products, represented as the mol % of styrene incorporated in the polymer (mol % styrene) was determined using FTIR spectroscopy. FTIR was performed on a Bruker Equinox 55+IR Scope II in reflection mode using a Pike MappIR accessory. 16 scans at 4 $cm^{-1}$ resolution were acquired. The IR spectra were analyzed by Partial Least Squares (PLS) analysis with PLSplus/IQ V3.04 for GRAMS/32 (Galactic Industries) software, using the following training set for calibration.

Training Set

The analysis based on a training set consisting of 180 spectra of blends of ethylene-styrene copolymers with known styrene incorporation, and atactic homo-polystyrene. The 16 known copolymers had between 1 and 47 mol % incorporated styrene. The atactic homo-polystyrene content in the blends ranged from 0 to 90% of the total styrene content of the blend. Most blends are prepared from copolymers with up to 20 mol % incorporation. Multiple spectra per blend were included in the training set.

Preprocessing of the Spectra

Mean centering; linear baseline correction based on average absorbances at 2074 $cm^{-1}$-2218 $cm^{-1}$ and 3224 $cm^{-1}$-3465 $cm^{-1}$; thickness correction based on band area from 1483 $cm^{-1}$ to 1504 $cm^{-1}$ with baseline from 1389 $cm^{-1}$-1413 $cm^{-1}$ to 1518 $cm^{-1}$--1527 $cm^{-1}$.

Analysis

PLS-1 algorithm; spectral regions 499 $cm^{-1}$ to 2033 $cm^{-1}$ and 3577 $cm^{-1}$ to 4495 $cm^{-1}$. Prediction of number ratios of atactic homo-polystyrene to total styrene ($\propto$ % atactic homo-polystyrene to total styrene) with 10 factors and ethylene to total styrene ($\propto$ mol % total styrene) with 7 factors and calculation of mol % incorporated styrene from these 2 numbers.

The training set of FTIR spectra used to develop this method comprised mostly of blends of polymers with less than 15 mol % styrene, and is most accurate in the range 1 mol % to 15 mol % incorporated styrene. Thus, for example, in Table 1 below, the mol % incorporated styrene by FTIR (PLS method) predicted mol % styrene below 15 mol % are shown to the nearest whole number, while predictions above 15 mol % are shown as >15 mol %. The mol % total styrene by linear regression is typically a more accurate measure of styrene content for high mol % incorporation, provided any atactic polystyrene is present at low levels, which is typically the case under these polymerization conditions for polymer yields of 40 mg or more.

The following ligands were used in some of these examples:

Ligand # 1

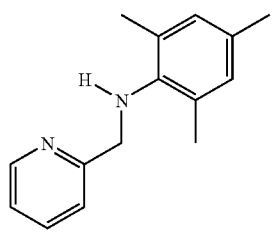

Ligand # 2

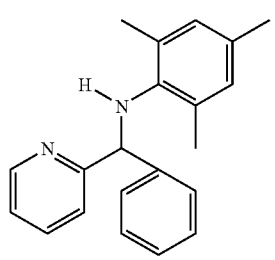

Ligand # 3

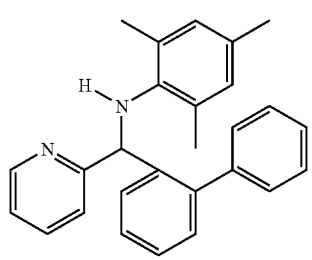

Ligand # 4

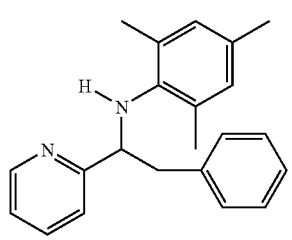

Ligand # 5

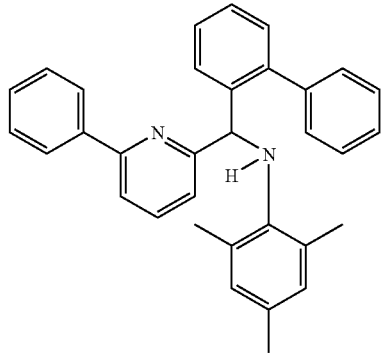

These ligands were prepared using techniques known to those of skill in the art. For example, using the following general experimental:

Part A: Synthesis of 2-bromo-6-formylpyridine

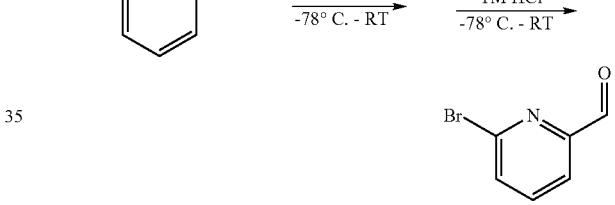

To a solution of 23.7 g (100 mmol) of 2,6-dibromopyridine in 150 mL of anhydrous, degassed THF cooled to −78° C. was added dropwise under $N_2$ a solution of 11.0 mL (110 mmol) of 10.0 M $^n$BuLi in 150 mL of anhydrous, degassed $Et_2O$. After 2 h at −78° C., 24.2 mL (300 mmol) of anhydrous, degassed DMF was added dropwise with rapid stirring. This solution was stirred at −78° C. for 2 h, then allowed to warm to RT overnight.

The solution was cooled to −78° C. and 100 mL of 1.0 M aq. HCl was added slowly. The organic phase was separated and the aqueous phase was washed with 3×50 mL $Et_2O$. The organic washes were combined and washed with 3×50 mL $H_2O$ and 3×50 mL brine, then dried over $Na_2SO_4$. The volatiles were removed in vacuo to provide an orange oil. The oil was triturated with hexanes to give a pale orange solid that was washed with cold pentane and dried under vacuum overnight.

Part B: Synthesis of 2-formyl-6-naphthylpyridine

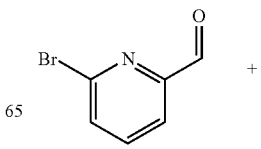

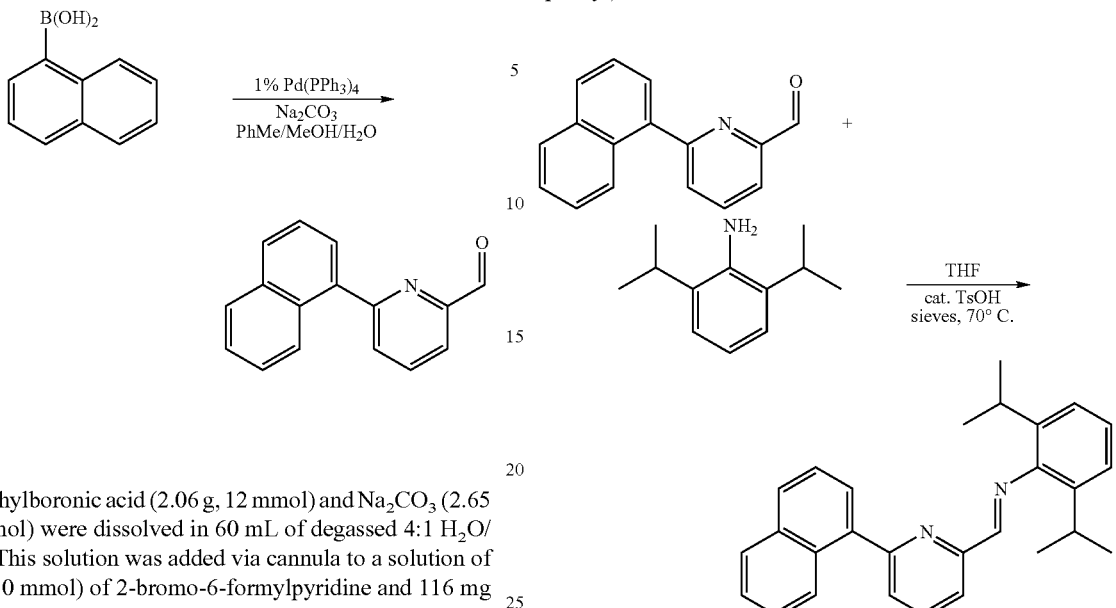

Part C: Synthesis of 6-naphthylpyridine-2-(2,6-diisopropylphenyl)imine

Naphthylboronic acid (2.06 g, 12 mmol) and Na$_2$CO$_3$ (2.65 g, 25 mmol) were dissolved in 60 mL of degassed 4:1 H$_2$O/MeOH. This solution was added via cannula to a solution of 1.86 g (10 mmol) of 2-bromo-6-formylpyridine and 116 mg (0.10 mmol) of Pd(PPh$_3$)$_4$ in 50 mL of degassed toluene. The biphasic solution was vigorously stirred and heated to 70° C. under N$_2$ for 4 h. On cooling to RT, the organic phase was separated and washed with 3×25 mL of Et$_2$O. The combined organic extracts were washed with 3×25 mL of H$_2$O and 1×20 mL of brine and dried over Na$_2$SO$_4$. After removing the volatiles in vacuo, the resultant brown oil was chromatographed on silica with 0-50% hexanes/CH$_2$Cl$_2$. The early fractions contained naphthalene and binaphthyl and were discarded. The remaining fractions were combined and the volatiles were removed to provide 2-formyl-6-naphthlypyridine as a white solid.

A solution of 1.17 g (0.5 mmol) of 2-formyl-6-naphtlypyridine and 0.98 g (0.55 mmol) of 2,6-diisopropylaniline in 50 mL of anhydrous THF containing 3 Å sieves and a catalytic amount of TsOH was heated to reflux under N$_2$ for 12 h. After filtration and removal of the volitiles in vacuo, the crude material was passed through a 4×6 cm plug of neutral alumina with 1:1 hexanes/CH$_2$Cl$_2$ eluent. Removal of the volitiles provided 6-naphthylpyridine-2-(2,6-diisopropylphenyl)imine as yellow crystals.

Part D: Synthesis of (6-naphthyl-2-pyridyl)-N-(2,6-diisopropylphenyl)benzylamine (Ligand L4)

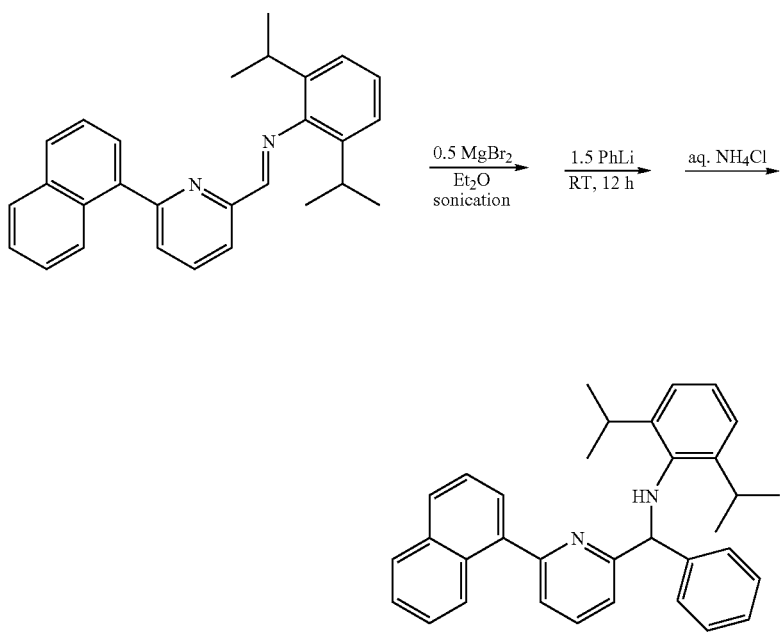

Synthesis With MgBr$_2$ Precomplexation:

To a well-stirred slurry of powdered MgBr$_2$ (184 mg, 1 mmol) in 2 mL of anhydrous, degassed Et$_2$O was added under N$_2$ a solution of 6-naphthylpyridine-2-(2,6-diisopropylphenyl)imirie (392 mg, 1 mmol) in 2 nmL of Et$_2$O. The mixture was s6nicated until the yellow color of the imine dissipated and a free-flowing pale yellow powder was formed. To this suspension was added with vigorous stirring a solution of phenyllithium (833 uL of 1.8 M in cyclohexane, 1.5 mmol). After stirring at RT for 12 h, the reaction was quenched with aq. NH$_4$Cl. The organic layer was separated, washed with brine and H$_2$O, then dried over Na$_2$SO$_4$. Following chromatography (silica gel, 3% THF/hexanes), the product was isolated as a colorless oil.

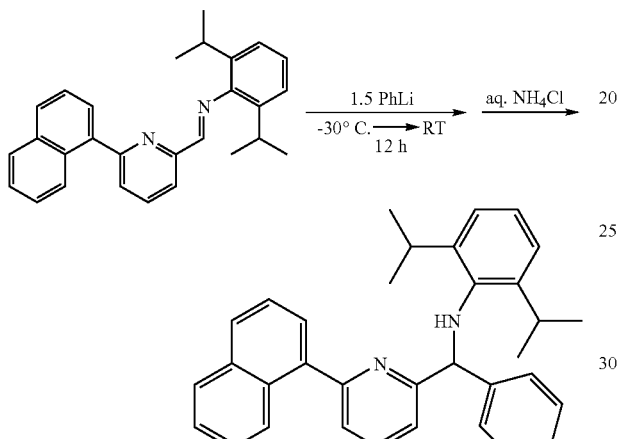

Synthesis Without MgBr$_2$ Precomplexation:

To a solution of 6-naphthylpyridine-2-(2,6-diisopropylphenyl)imine (392 mg, 1 mmol) in 5 mL of anhydrous, degassed Et$_2$O cooled to −30° C. under N$_2$ was added a solution of phenyllithium (833 uL of 1.8 M in cyclohexane, 1.5 mmol). After warming to RT over 1 h. the soln. was stirred at RT for 12 h. The reaction was then quenched with aq. NH$_4$Cl, and worked-up as above.

For ligand L#1-L#4, part A and part B were not used. For part C, 2-pyridinecarboxyaldehyde (commercial from Aldrich) was used as starting material.

Part C:

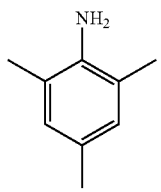

Part D:

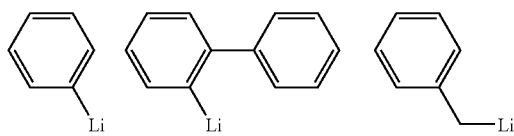

For:  L#2  L#3  L#4

For ligand L#1, the last step in the reaction sequence (part D) is a reduction reaction using sodiumtriacetozyborohydride (Na(OAc)$_3$BH) in THF for 1-3 days following aq. NH$_4$Cl quench and work-up as it is described in Part D above.

These procedures are followed for ligand L#5, but with the following different starting materials:

Part B:

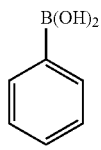

Part C:

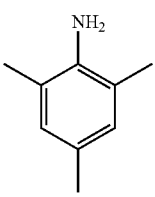

Part D:

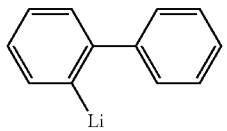

Example 1

Synthesis of Ligand 2

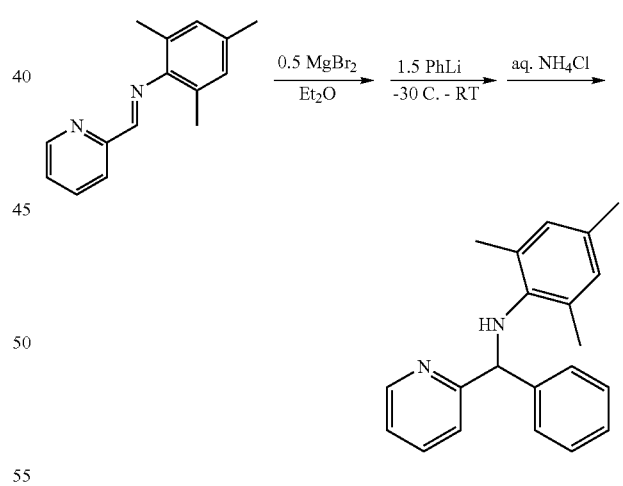

Both parts to this example make the same ligand, shown above, with and without the presence of complexing agent.

Part A: Synthesis without MgBr$_2$ Complexation:

To a solution of 2-pyridyl-N-mesitylimine (224 mg, 1 mmol) in 5 mL of anhydrous, degassed Et$_2$O cooled to −30° C. was added under argon a solution of phenyllithium (833 μL of 1.8 M in cyclohexane, 1.5 mmol). After warming to room temperature over 1 hour, the solution was stirred for a further 12 hours. The reaction was then quenched with aqueous NH$_4$Cl, the layers were separated, and the organic layer was dried over Na$_2$SO$_4$. GC-MS analysis showed a mixture of the C- and N-alkylated products. The C- to N-alkylation ratio was 4:1 as determined by $^1$N NMR.

Part B: Synthesis with MgBr$_2$ Complexation:

To a stirred slurry of powdered MgBr$_2$ (92 mg, 0.5 mmol) in 1 mL of anhydrous, degassed Et$_2$O was added under argon a solution of 2-pyridyl-N-mesitylimine (224 mg, 1 mmol) in 5 mL of Et$_2$O. The mixture was stirred for 2 hours until the yellow color of the imine dissipated and a pale yellow solid was formed. After cooling to −30° C., a solution of phenyllithium (833 uL of 1.8 M in cyclohexane, 1.5 mmol) was added with stirring. After warming to room temperature over 1 hour, the solution was stirred for a further 12 hours. The reaction was worked up as above. GC-MS analysis showed exclusive formation of the C-alkylated product. Following chromatography (silica, 10% ethyl acetate/hexanes), the product was isolated as a colorless solid (266 mg, 88%).

Example 2

Synthesis of Titanium-Ligand Complexes C1-C4

Ti(NMe$_2$)$_4$ was purchased from Strem Chemicals. Ti(NMe$_2$)Cl$_2$ and Ti(NMe$_2$)I$_2$ were prepared by the modification of Ti(NMe$_2$)$_4$ with 2 equivalents of trimethylsilylchloride and trimethylsilyliodide, respectively. Ti(CH$_2$Ph)$_4$ was preparead by modification of TiCl$_4$ with 4 equivalents of benzylmagnesium chloride in an ether/hexane mixture.

The following 4 metal complexes were prepared. In each case the ligand was synthesized following the general methodology set forth in Example 1, above.

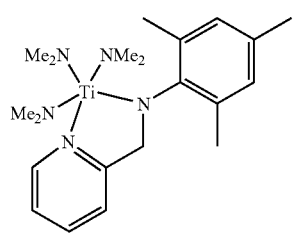

C1

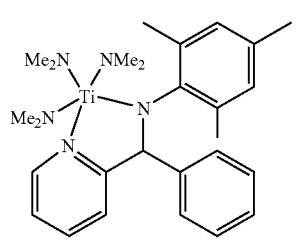

C2

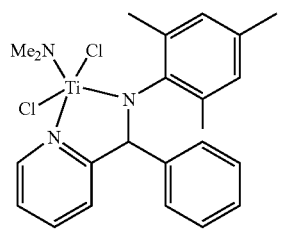

C3

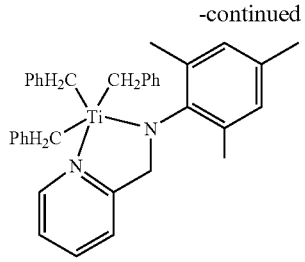

C4

Complex C#1: Ligand 1 (103 mg, 0.48 mmol) and Ti(NMe2)4 were combined and 4 mL C$_6$D$_6$ was added. The yellow mixture was stirred at room temperature for 2 hours, at which time solvent was removed. The yellow solid was recrystallized from pentane at −35C. Yellow crystals were collected, washed with pentane, and dried. (yield =136 mg, 73%) $^1$N NMR was consistent with the structure shown for Cl.

Complex C#2: In a manner similar to that descirbed for C1, complex C2 was prepared from Ligand 2 (493 mg, 1.62 mmol) and Ti(NMe$_2$)$_4$ (385 mg, 1.71 mmol). Yellow crystals were obtained upon recrystallization from pentane at −35C. (yield=765 mg, 98%) $^1$N NMR was consistent with the structure shown for C2.

Complex C#3: Ligand 2 (192 mg, 0.63 mmol) and Ti(NMe$_2$)$_2$Cl$_2$ (135 mg, 0.65 mmol) were combined and 4 mL C$_6$D$_6$ was added. The mixture was stirred for 2 hours, solvent was removed, and pentane (10 mL) was added to the solid product. The mixture was stored at −35 C overnight, and then the precipitate was collected, washed with pentane and dried. (yield=175 mg, 59%) $^1$H NMR was consistent with the structure shown for C3.

Complex C#4: Ligand 1 and Ti(CH$_2$Ph)$_4$ were combined in C$_6$D$_6$ and allowed to stir overnight in the absence of light. Solvent was removed, leaving a red-brown oil, which was recrystallized from pentane at−35C. $^1$H NMR was consistent with the structure shown for C4.

Examples 3-4

Preparation of the polymerization reactor prior to injection of catalyst composition: A pre-weighed glass vial insert and disposable stirring paddle were fitted to each reaction vessel of the reactor. The reactor was then closed, 0.10 mL of a 0.02 M solution of group 13 reagents in toluene and 3.8 mL of toluene were injected into each pressure reaction vessel through a valve. The temperature was then set to 110° C., and the stirring speed was set to 800 rpm, and the mixture was exposed to ethylene at 100 psi pressure. A ethylene pressure of 100 psi in the pressure cell and the temperature setting were maintained, using computer control, until the end of the polymerization experiment.

Preparation of the group 13 reagent and activator stock solutions: The "activator solution" is a 5 mM solution of N,N'-dimethylanilinium tetrakis (pentafluorophenyl) borate in toluene ("ABF20") or a toluene solution which is 5 mM in N,N'-dimethylanilinium tertakis(pentafluorophenyl) borate and 10 mM in tris(pentafluorophenyl) borane ("cocktail"). The solution is heated to approximately 85° C. to dissolve the reagent. The "group 13 reagent" solution is either a 0.2 M solution of triisobutylaluminium ("TIBA") or a 0.2 M solution of Akzo polymethylaluminoxane-improved process PMAO-IP ("PMAO"), all "group 13 reagent" solutions were solutions in toluene.

Polymerization: The polymerization reaction was allowed to continue for 10-30 min, during which time the temperature and pressure were maintained at their pre-set levels by computer control. The polymerization times are given in the table of each example as "Run time". After the reaction time elapsed, the reaction was quenched by addition of an overpressure of carbon dioxide.

Product work up: ethylene/styrene copolymerizations After the polymerization reaction, the glass vial insert, containing the polymer product and solvent, was removed from the pressure cell and removed from the inert atmosphere dry box, and the volatile components were removed using a centrifuge vacuum evaporator. After most of the volatile components had evaporated, the vial contents were dried thoroughly by evaporation at elevated temperature under reduced pressure. The vial was then weighed to determine the yield of polymer product. The polymer product was then analyzed by rapid GPC, as described above to determine the molecular weight of the polymer produced, and by FTIR spectroscopy to determine the styrene incorporation.

Example 3

Ethylene-Styrene Polymerizations using Titanium Precursor-Ligand Compositions

Five polymerization reactions were carried out with different ligand/metal compositions for the copolymerization of ethylene and styrene. Additional experimental details are described in table 1.

In situ preparation of Titanium-ligand compositions: Stock solutions were prepared as follows: The "metal precursor solution" is a 10 mM solution of $Ti(CH_2C_6H_5)_4$ in toluene ($TiCl_4$ was modified with 4 equivalents of benzyl Gringard at −30° C. in ether) or a 10 mM solution of $Ti(NMe_2)_2Cl_2$ in toluene ($Ti(NMe_2)_2$ was modilfied with 2 equivalents of TMS-Cl).

For the ligand-$Ti(NMe_2)_2Cl_2$ compositions, 0.75 μmol ligand in 0.030 mL toluene were mixed with 0.075 ml of the 10 mM metal precursor solution in a 1 ml vial. The resultant solutions we allowed to sit at 90° C. for 75 min (as described in table 1 as complexation temperature and complexation time). The reaction mixtures were dried completely by blowing a stream of Argon over the 1 ml vial. A small amount of toluenen was added (0.02 mL) befor eany subsequent addition of reagents.

For the ligand-$Ti(CH_2C_6H_5)_4$ compositions, 0.75 μmol ligand in 0.060 mL toluene were mixed with 0.075 ml of the 10 mM metal precursor solution in a 1 ml vial. The resultant solutions we allowed to sit at a complexation temperature and complexation time as indicated in table 1. The reaction mixtures were used without further work-up.

Injection of solutions into the pressure reactor vessel: To the ligand metal composition, 0.030 mL −0.040 mL of a 500 mM solution of 1-octene in toluene was added. Then, an appropriate amount of the group 13 reagent solution was added to the 1 mL vial (the amount can be calculated from the Premix group 13 reagent/Ti ratio in table 1 and the concentration of the used group 13 reagent stock solution). This mixture was held for a time ti as indicated in table 1, during which time, 0.420 mL of styrene followed immediately by 0.380 mL of toluene, were injected into the prepressurized reaction vessel. Then, 0.165 mL (0.825 μmol) of the "activator solution" was added to the 1 mL vial. After the time period $t_2$ elapsed ($t_2$ as indicated in table 1), a fraction of the total 1 mL vial contents equivalent to 0.5 μmol Ti, followed immediately by approximately 0.6 mL of toluene were injected into the reaction vessel.

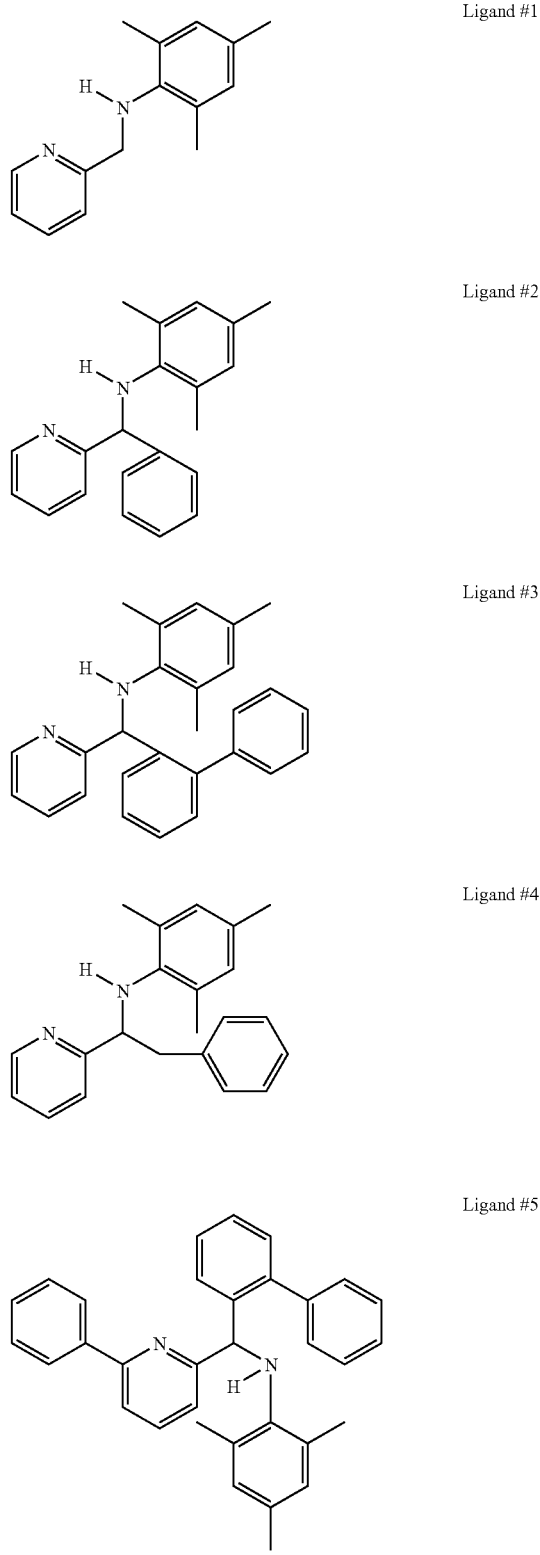

Ligand #1

Ligand #2

Ligand #3

Ligand #4

Ligand #5

TABLE 1

|  | Example # | | | | |
| --- | --- | --- | --- | --- | --- |
|  | 3.1 | 3.2 | 3.3 | 3.4 | 3.5 |
| Metal Precursor | $Ti(NMe_2)_2Cl_2$ | $Ti(NMe_2)_2Cl_2$ | $TiBz_4$ | $TiBz_4$ | $TiBz_4$ |
| Ligand # | 2 | 3 | 4 | 4 | 5 |
| Complexation Time | 75 min. | 75 min. | 120 min. | 45 min. | 90 min. |
| Complexation Temperature | 90° C. | 90° C. | 25° C. | 70° C. | 25° C. |
| group 13 reagent | TIBA | TIBA | PMAO | PMAO | TIBA |
| Premix group 13 reagent/Ti ratio | 20/1 | 20/1 | 5/1 | 5/1 | 6/1 |
| $t_1$ (min) | 10 | 10 | 1 | 1 | 10 |
| $t_2$ (sec) | 30 | 30 | 30 | 30 | 30 |
| Activator(s) | ABF20 | ABF20 | ABF20 | ABF20 | ABF20 |
| μmol Ti | 0.5 | 0.5 | 0.5 | 0.5 | 0.5 |
| Run Time (min.) | 15 | 15 | 15 | 30 | 15 |
| Polymer Yield (mg) | 104 | 74 | 40 | 71 | 33 |
| Activity (mg polymer per μmol per min.) | 14 | 10 | 5 | 5 | 4 |
| mol % incorporated styrene by FTIR (PLS method) | >15 | >15 | >15 | 13 | >15 |
| Mol % total styrene by FTIR (linear regression) | 18 | 17 | 15 | 14 | 15 |
| Mw (k) | 160 | 145 | 423 | 448 | 411 |
| Mw/Mn | 1.9 | 3.1 | 4.1 | 2.7 | 2.6 |

Herein "Bz" refers to benzyl.

Example 4

Ethylene-Styrene Copolymerization with Isolated Metal-Ligand Complexes:

Six polymerization reactions were carried out with different metal-ligand complexes for the copolymerization of ethylene and styrene. Polymerization experiments were carried out in a manner similar to Example 3, above, without the use of a in-situ preparation step. Additional experimental details are described in table 2.

Injection of Solutions into the Pressure Reactor Vessel:

Example 4.1

First, 0.30 mL of a 500 mM solution of 1-octene in toluene was dispensed in a 1 mL vial. Then, 0.075 mL of the 0.2 M group 13 reagent solution was added. Then 0.150 mL of a 5 mM (0.75 μmol) complex solution was added followed by 0.020 ml toluene. This mixture was held for 10 minutes, during which time, 0.420 mL of styrene followed immediately by 0.380 mL of toluene were injected into the prepressurized reaction vessel. Then, 0.165 mL (0.825 μmol) of the "activator solution" was added to the 1 mL vial. After 30 seconds, 0.295 mL of the total 1 mL vial contents equivalent to 0.5 μmol Ti, followed immediately by approximately 0.5 mL of toluene were injected into the reaction vessel.

Example 4.2.-4.6.

First, appropriate amount of the 0.2 M group 13 reagent solution was dispensed in a 1 mL vial. Then 0.120 mL of a 5 mM (0.6 μmol) complex solution was added. This mixture was held for 10 minute, during which time, 0.420 mL of styrene followed immediately by 0.380 mL of toluene were injected into the prepressurized reaction vessel. Then, 0.132 mL (0.66 μmol) of the "activator solution" was added to the 1 mL vial. After 30 seconds, 0.209 mL of the total 1 mL vial contents corresponding 0.4 μmol Ti, followed immediately by approximately 0.6 mL of toluene were injected into the reaction vessel.

TABLE 2

Ethylene-Styrene Copolymerization Experiments using isolated complexes.

|  | Example # | | | | | |
| --- | --- | --- | --- | --- | --- | --- |
|  | 4.1 | 4.2 | 4.3 | 4.4 | 4.5 | 4.6 |
| Complex # | 1 | 2 | 2 | 2 | 2 | 3 |
| group 13 reagent | TIBA | TIBA | TIBA | TIBA | TIBA | TIBA |
| Premix group 13 reagent/Ti ratio | 20/1 | 15/1 | 30/1 | 15/1 | 30/1 | 15/1 |
| Activator | cocktail | ABF20 | ABF20 | cocktail | cocktail | ABF20 |
| μmol Ti | 0.5 | 0.4 | 0.4 | 0.4 | 0.4 | 0.4 |
| Run Time (min.) | 10 | 15 | 15 | 15 | 15 | 15 |
| Polymer Yield (mg) | 46 | 88 | 61 | 70 | 64 | 48 |
| Activity (mg polymer per μmol per min.) | 9 | 15 | 10 | 12 | 11 | 8 |
| Mol % incorporated styrene by FTIR (PLS method) | 5 | 11 | 11 | 9 | 11 | >15 |
| mol % total styrene by FTIR (linear regression) | 9 | 12 | 13 | 12 | 12 | 18 |

TABLE 2-continued

Ethylene-Styrene Copolymerization Experiments using isolated complexes.

| | Example # | | | | | |
|---|---|---|---|---|---|---|
| | 4.1 | 4.2 | 4.3 | 4.4 | 4.5 | 4.6 |
| Mw (k) | 149 | 200 | 142 | 176 | 163 | 180 |
| Mw/Mn | 3.8 | 2.0 | 2.6 | 2.1 | 2.1 | 2.5 |

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated herein by reference for all purposes.

What is claimed is:

1. A composition comprising:
   (1) a ligand characterized by the following general formula:

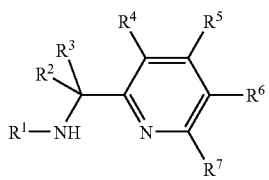

wherein $R^1$ is selected from the group consisting of alkyl, substituted alkyl, cycloalkyl, substituted cycloalkyl, heteroalkyl, substituted heteroalkyl, heterocycloalkyl, substituted hetercycloalkyl, aryl, substituted aryl, heteroaryl, or substituted heteroaryl; $R^2$, $R^3$, $R^4$, $R^5$, $R^6$, and $R^7$ are independently selected from the group consisting of hydrogen, alkyl, substituted alkyl, cycloalkyl, substituted cycloalkyl, heteroalkyl, substituted heteroalkyl, heterocycloalkyl, substituted hetercycloalkyl, aryl, substituted aryl, heteroaryl, substituted heteroaryl, alkoxyl, aryloxyl, silyl, boryl, phosphino, amino, thio, seleno, nitro, and combinations thereof;
   (2) a metal precursor compound characterized by the general formula $Ti(L)_n$ where each L is independently selected from the group consisting of halide, alkyl, substituted alkyl, cycloalkyl, substituted cycloalkyl, heteroalkyl, substituted heteroalkyl heterocycloalkyl, substituted heterocycloalkyl, aryl, substituted aryl, heteroaryl, substituted heteroaryl, alkoxy, aryloxy, hydroxy, boryl, silyl, amino, amine, hydrido, allyl, diene, seleno, phosphino, phosphine, ether, thioether, carboxylates, thio, 1,3-dionates, oxalates, carbonates, nitrates, sulphates, ethers, thioethers and combinations thereof; optionally two or more L groups are combined in a ring structure having from 3 to 50 non-hydrogen atoms; n is 1, 2, 3, 4, 5, or 6; and
   (3) optionally, at least one activator.

2. The composition of claim 1 wherein $R^7$ is hydrogen.

3. The composition of claim 1 wherein $R^1$ is mesityl.

4. A composition comprising:
   (1) a ligand characterized by the following general formula:

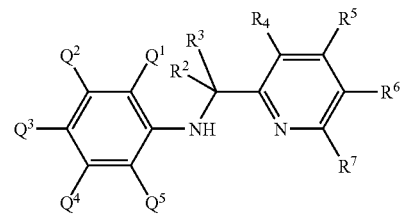

wherein $Q^2$, $Q^3$, $Q^4$, $R^2$, $R^3$, $R^4$, $R^5$, $R^6$, and $R^7$ are independently selected from the group consisting of hydrogen, alkyl, substituted alkyl, cycloalkyl, substituted cycloalkyl, heteroalkyl, substituted heteroalkyl, heterocycloalkyl, substituted hetercycloalkyl, aryl, substituted aryl, heteroaryl, substituted heteroaryl, alkoxyl, aryloxyl, silyl, boryl, phosphino, amino, thio, seleno, nitro, and combinations thereof; $Q^1$ and $Q^5$ are selected from the group consisting of alkyl, substituted alkyl, cycloalkyl, substituted cycloalkyl, aryl, substituted aryl;
   (2) a metal precursor compound characterized by the general formula $Ti(L)_n$ where each L is independently selected from the group consisting of halide, alkyl, substituted alkyl, cycloalkyl, substituted cycloalkyl, heteroalkyl, substituted heteroalkyl heterocycloalkyl, substituted heterocycloalkyl, aryl, substituted aryl, heteroaryl, substituted heteroaryl, alkoxy, aryloxy, hydroxy, boryl, silyl, amino, amine, hydrido, allyl, diene, seleno, phosphino, phosphine, ether, thioether, carboxylates, thio, 1,3-dionates, oxalates, carbonates, nitrates, sulphates, and combinations thereof; n is 1, 2, 3, 4, 5, or 6; and
   (3) optionally, at least one activator.

5. The composition of claim 4, wherein $R^3$ is selected from the group consisting of aryl, and substituted aryl, heteroaryl, substituted heteroaryl; and $R^7$ is selected from the group consisting of hydrogen, aryl, and substituted aryl.

6. The composition of claim 4, wherein $Q^1$, $Q^3$ and $Q^5$ are each methyl and $Q^2$ and $Q^4$ are each hydrogen.

7. The composition of claim 4, wherein said ligand is selected from the group consisting of

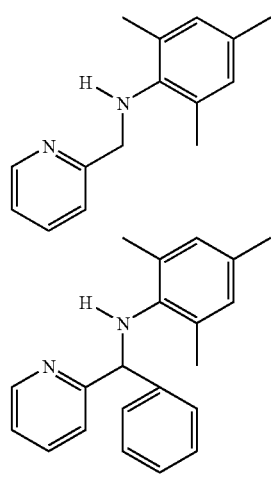

-continued
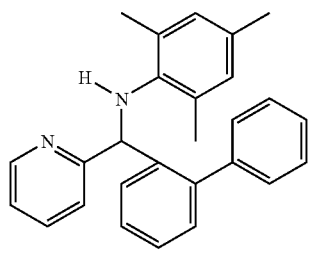
-continued
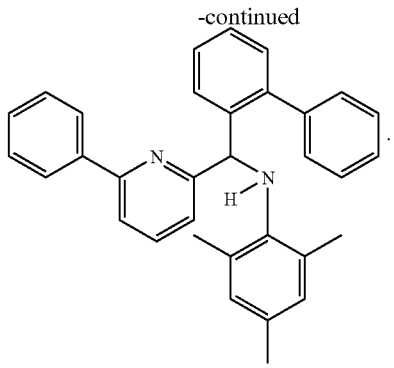
* * * * *